US006573428B1

(12) United States Patent
Vodkin et al.

(10) Patent No.: US 6,573,428 B1
(45) Date of Patent: Jun. 3, 2003

(54) SOYBEAN PROMOTER EXPRESSED PREFERENTIALLY IN PODS

(75) Inventors: Lila Vodkin, Champaign, IL (US); Martina Stromvik, St. Anthony, MN (US); Vijaya Sundararaman, Malvern, PA (US)

(73) Assignee: Board of Trustees of the University of Illinois, Urbana, IL (US)

( * ) Notice: Subject to any disclaimer, the term of this patent is extended or adjusted under 35 U.S.C. 154(b) by 0 days.

(21) Appl. No.: 09/694,127

(22) Filed: Oct. 20, 2000

Related U.S. Application Data
(60) Provisional application No. 60/160,720, filed on Oct. 20, 1999.

(51) Int. Cl.[7] .............................. C10N 5/04; C10N 5/10; C10N 15/52; C10N 15/32; C10N 15/56; C10N 15/29; A01H 5/00; A01H 5/10
(52) U.S. Cl. ................... 800/287; 536/24.1; 536/23.71; 536/23.2; 800/279; 800/278; 800/288; 800/298; 800/301; 800/302; 800/317.4; 800/313; 800/312; 800/317; 435/418; 435/419; 435/411; 435/415; 435/320.1; 435/468; 435/430; 435/200
(58) Field of Search .............................. 536/24.1, 23.71, 536/23.2; 800/279, 278, 287, 288, 298, 301, 302, 312, 313, 317.4, 317; 435/200, 320.1, 418, 419, 411, 415, 468, 430

(56) References Cited

FOREIGN PATENT DOCUMENTS
WO    WO 97/37023    10/1997

OTHER PUBLICATIONS

Cook, ABC of Plant Terms, Merrow Publishing, Ltd., Durham, England, 1968, p. 255.*
Mahairas G. G. AQ091364 Aug. 26, 1998.*
Broomall et al. *Pneumocystis carinii* promoter analysis in a heterologous saccharomyces cervisiae assay system vol. 44 No. 6, Nov.–Dec. 1997.*
Wada et al. MSG Gene cluster encoding major cell surface glycoproteins of rat *pneumocystis carinii* DNA research 1, 163–168 1994 No. 4.*
Williams et al. The chromosomal location of a gene (msg) affecting megasporogenesis in durum wheat 578–581 Genome Aug. 1987 No. 4.*
Watahiki et al. The MSG1 and AXR1 genes of arabidposis are likely to act independently in growth–curvature responses of hypocotyls Planta 1999 207: 362–369 Jan No. 3.*
Donald et al. Mutation of either G box or I box sequences profoundly affects expression from the arabifopsis rbcS–1A promoter EMBO journal vol. 9 No. 6pp.1717–1726, 1990.*
Aggelis et al. (1997) "Characterization of two cDNA clones for mRNAs expressed during ripening of melon (*Cucumis melo* L.) Fruits," *Plant Mol. Biol.* 33:313–322.

Breiteneder et al. (1993) "Four recombinant isoforms of Cor a I, the major allergen of hazel pollen, show different IgE–binding properties," *Eur J. Biochem.* 212:355–362.
Breiteneder et al. (1995) "Molecular characterization of Api g 1, the major allergen of celery (*Apium graveolens*), and its immunological and structural relationships to a group of 17–kDa tree pollen allergens," *Eur. J. Biochem.* 233:484–489.
Bustos et al. (1989) "Regulation of β–Glucuronidase Expression in Transgenic Tobacco Plants by an A/T Rich, cis–Acting Sequence Found Upstream of a French Bean β–Phaseolin Gene," *Plant Cell* 1:839–853.
Bustos et al. (1991) "Positive and negative cis–acting DNA domains are required for spatial and temporal regulation of gene expression by a seed storage protein promoter," *EMBO J.* 10:1469–1479.
Czarnecka et al. (1992) "AT–rich promoter elements of soybean heat shock gene Gmhsp 17.5E bind two distinct sets of nuclear proteins in vitro," *Plant Mol. Biol.* 19:985–1000.
Eyal et al. (1993) "A basic–type PR–1 promoter directs ethylene responsiveness, vascular and abscission zone–specific expression," *Plant J.* 4:225–234.
GenBank Accession No. X79230 (Feb. 1999) *Capsicum annuum* (Yolo Wonder) Sn–1 gene.
GenBank Accession No. S44872 (May 1993) *Nicotiana tabacum=tobacco, cv Samsun nn, floral bud day 7 explant, mRNA, 691 nt*.
GenBank Accession No. AJ239237 (Nov. 1999) *Glycine max msg gene, exons 1–2*.
GenBank Accession No. Z70522 (Feb. 1997) *Cucumis melo mRNA (clone pMe17)*.
GenBank Accession No. S28427 (Nov. 1999) *Major latex protein (clone gMPL22)–opium poppy*.
Griffing and Nessler (1989) "Immunolocalization of the Major Latex Proteins in Developing Laticifers of Opium Poppy (*Papaver somniferum*)," *J. Plant Physiol.* 134:357–363.

(List continued on next page.)

Primary Examiner—David T. Fox
Assistant Examiner—Anne Kubelik
(74) Attorney, Agent, or Firm—Greenlee Winner and Sullivan, PC

(57) ABSTRACT

This application discloses the tissue-specific transcription regulatory sequences from the soybean Msg, gene, which is highly expressed in tissues which are potential sites of entry of plant pathogens or attack by plant pests, including the developing soybean pods. The Msg gene shows significant homology to a family of fruit and flower specific genes, designated the major latex protein (MLP) homologs, so far reported in only a few species and whose functions are unknown. The Msg transcription regulatory sequences are fully active in Arabidopsis only in plants transformed with the 2.26 kb fragment promoter, expressing an associated coding sequence in nectaries, nodes, short style and in guard cells of the silique, pedicel and stem but not in mature leaves. Methods for tissue specific sequence expression are provided in the present application.

45 Claims, 12 Drawing Sheets

OTHER PUBLICATIONS

Klich (1990) "The degree of Susceptibility of Nectary–Inoculate Cotton Flowers and Bolls to Subsequent Seed Infection by *Aspergillus flavus* Is Determined at or before Anthesis," *Appl. Environ. Microbiol* 56:2499–2502.

Marcus et al. (1997) "Purification, characterisation and cDNA cloning of an antimicrobial peptide from *Macadamia intergrifolia*," *Eur. J. Biochem.* 244:743–749.

Meeks–Wagner et al. (Jan. 1989) "Tobacco Genes Expressed during in Vitro Floral Initiation and Their Expression during Normal Plant Development," *Plant Cell* 1:25–35.

Moiseyev et al (1997) "Primary structures of two ribonucleases from ginseng calluses," *FEBS Lett.* 407:207–210.

Nam et al. (Feb. 1999), "Isolation and characterization of mRNAs differentially expressed during ripening of wild strawberry (*Fragaria vesca* L.) Fruits," *Plant Mol. Biol.* 39:629–636.

Neale et al. (Jul. 19990) "Chitinase, β–1–3–Glucanase, Osmotin, and Extensin Are Expressed in Tobacco Explants during Flower Formation," *Plant Cell* 2:673–684.

Nessler et al. (1990) "Cloning and expression analysis of DNA sequences for the major latex protein of opium poppy," *Planta* 180:487–491.

Nessler et al. (1990) "Isolation and analysis of the major latex protein genes of opium poppy," *Plant Mol. Biol.* 15:951–953.

Nessler and Burnett (1992) "Organization of the major latex protein gene family in opium poppy," *Plant Mol. Biol.* 20:749–752.

Nessler, C.L. (1994) "Sequence analysis of two new members of the major latex protein gene family supports the triploid–hybrid origin of the opium poppy," *Gene* 139:207–209.

Pozueta–Romero et al. (1995) "Characterization of a family of genes encoding a fruit–specific wound–stimulated protein of bell pepper (*Capsicum annuum*): identification of a new family of transposable elements," *Plant Mol. Biol.* 28:1011–1025.

Rao, A.G. (1995) "Antimicrobial Peptides," *Mol. Plant–Microbe. Interact.* 83:6–13.

Rushton et al. (1996) "Interaction of elicitor–induced DNA–binding proteins with elicitor response elements in the promoters of parsley PR1 genes," *EMBO J.* 15:5690–5700.

Sandhu et al. (Jul. 1998) "A/T–rich sequences act as quantitative enhancers of gene expression in transgenic tobacco and potato plants," *Plant Mol. Biol.* 37:885–896.

Saravitz, D.A. and Siedow, J.N., (1996), "The Differential Expression of Wound–Inducible Lipoxygenase Genes in Soybean Leaves," *Plant Physiol.* 110:287–299.

Schöffl et al. (1984) "The DNA sequence analysis of soybean heat–shock genes and identification of possible regulatory promoter elements," *EMBO J.* 3:2491–2497.

Segura et al. (Jan. 1999) "Snakin–1, a Peptide from Potato That Is Active Against Plant Pathogens," *Mol Plant Microbe Interact* 12:16–23.

Stromvik et al. (Sep. 1999) "A novel promoter from soybean that is active in a complex developmental pattern with and without its proximal 650 base pairs," *Plant Mol. Biol.* 41:217–231 [Date available Oct. 25, 1999, per publisher].

Singh, K.B. (1998) "Transcriptional Regulation in Plants: The Importance of Combinatorial Control," *Plant Physiol* 118:1111–1120.

Thoma et al (1994) "Tissue–Specific Expression of a Gene Encoding a Cell Wall–Localized Lipid Transfer Protein from Arabidopsis[1]," *Plant Physiol* 105:35–45.

Wada, M. and Yoshikazu N., (1994), "MSG Gene Cluster Encoding Major Cell Surface Glycoproteins of Rat *Pneumocystis carinii*," *DNA Research* 1(4):163–168.

Wieczorek et al. (May 1998) "Function of $TAF_{II}$–containing complex without TBP in transcription by RNA polymerase II," *Nature* 393:187–191.

Zhong et al., (1997), "A 28–Kilodalton Pod Storage Protein of French Bean Plants[1]," *Plant Physiol.* 113:479–485.

* cited by examiner

```
+327   TGATTTGATGATGAAAACAAGAAGATAAACCTACACCATATATTGGAGGGTGTCATGTTGAAGTACTATAAGAGACTACAAGGTTATCGTTCATGTTTACCA   2700
         D  F  D  D  E  N  K  K  I  T  Y  T  I  L  E  G  V  M  L  K  Y  Y  K  S  Y  K  V  I  V  H  V  L  P

+427   AAAGGTGATGAGCACAGCCTTGTGGTGAAGTGGACTTTCTTGTATGAGAAGGTGGATCACACTGCCCCTGAGCCAACCAAGTACAAAGATTGGTGGTTAAAC   2800
         K  G  D  E  H  S  L  V  K  W  T  F  L  Y  E  K  V  D  H  T  A  P  E  P  T  K  Y  K  D  L  V  V  K

+527   TCACCAAGAACGTGGAGGCTCATCTTGTTGAGGCTC GTT AAAATGATCCCTAAGTGGTTCACGC TAAAT AAAGTTGTGATGTGTGGTGTGTTGCATGT   2900
         L  T  K  N  V  E  A  H  L  vSstEl                                      polyA signal
                                     A  R
                                MSG3UTRFor +627   GGCCCCTTGGTTAATTATCAGCCATTATGTTTGCTTTAAATTGCCGTGCGTAATATGTTGTTGGTTAACTTGTTAAAAATATTGGTTCTCAACCATAAGT   3000
                                                                                                    HincII +727   TGTGTAATGTGTTGTTGGTTTATTCAAAATATTGGCCGGGATCACAGGGAGGCTACACAGCTTGTGATTTGTAATCTCTGTGATTTCTGACCAGCTAT   3100

+827   TGATTAATTGATGTTAAGGGGGATTTATCCTTGTTGTCTCAAACATTTTGCCAAATACTTTTGATAACTAGAAGGTTTGTGGATAGCCGGTTTTCTTC   3200

+927   ATTGGGAAGCTTACAGGCATGGCTAAAAACCAGAA GAATTAATTAAATGCTTCCACAAAAGTTGTTAATTAAATTAAACACTTGAATA   3300
                                         MSG3UTRRev         EcoRI

+1027  TGTTT AAGCTT TGAAAAA T TACAGATCTTGCATTTGATATTTAATAATTCTTCTTAACTTTTGATTCCTGAAAAATATTTTATATTGATTCTTG   3400
            HindIII  SphI
```

FIG. 3C

```
                         1               15 16              30 31              45
1. Capsicum annuum (Sn-1)      ----------      ---------MGVKGKL IASVEVKCEGNLIHE LFHIHA-HHVPNISP
2. Nicotiana tabacum (FB7-4)   ----------      ---------MGLKGKL IAQIEMKCAGDLLHE HFKSNP-HQTSTMSP
3. Glycine max (MSG)           ----------      ---------MSQPDSL VAEIEVKTSADHFYD TLKGKKQHRIHDVAP
4. Cucumis melo (MEL7)         ----------      ---------MSLIGKL VSELEINAAAEKFYE IFKDQC-FQVPNITP
5. Papaver somniferum (MLP 22) MAEHHHTISGLVGKL VTELEVNCNADEYYK IFKHH--EDLPNAIP 46              60 61              75 76              90 91             105 106             120
1. NFINHFEIHEGETVK VG--SVVSWSYNEAG QKRYMKQLIEDIDPD MKLIFWKAIEGDVLE SYNSFTIVT----S
2. NKITNFTLHEGQLGS TG--SVVSWKFVLGG KERHAKQVLH-IDDA KKSITFNFVEGDMNE LYKSMTATL----T
3. HHIHKVEVHEGEWDK SGN--IKVLTFADGD TVETLKERV-DFDDE NKKITYTILEGVMLK YYKSYKVIVHVLPKG
4. RCIQQVEIHGTNWDG HGHGSIKSWYYTIDG KAEVFKERV-EFHDD KLLIVLDGVGGDVFK NYKSFKPAYQFVPKD
5. HIYRGVAVEGDRIT  SGF--IKEWHYIIEG KPLTCKERTT-YEDE ARTIHHSTVEGVLLD DYKKFDATLVNPKAD 121             135 136             150 151             165
1. SEHEWTTWTIEYEKK TEGTPEPLVLLGLVL DMTKDIEAHLLKK-- 147
2. AEGNWMTWTFVYEKL NENIPEPLDIFELAI CLLKDLEPHHVGK-- 146
3. DEHSLVKWTFLYEKV DHTAPEPTKYKDLVV KLTKNVEAHLVEAR  153
4. RNHCQAILSIEYEKL HHGSPDPHKYIDLMI GITNDIGSHIK---  151
5. GHGSIVTWIVEYEKI NEDSPVPISYLTFH- KIIEDLNTYLCASD  158
```

FIG. 4

The *Msg* gene and flanking genomic sequence (kb)

SEQUENCE LISTING

<160> NUMBER OF SEQ ID NOS: 19

<210> SEQ ID NO 1
<211> LENGTH: 3400
<212> TYPE: DNA
<213> ORGANISM: Glycine max

<400> SEQUENCE: 1

```
tccattgtgg aaacccgacg agtttaatca caagcacaac gagttaaaat gattttgaaa      60
ataattgagt agttgtgtgt attgcatagt tcataggtaa agtgtgtgtg attcatgaaa     120
tgtgatgaca tgttaaattg agattatact attgtgattg agatcgagtg tatgtgataa     180
attgagtatg tacgtgattg tgatgttgtt tgcattgagt tatgaactat gaattgtaca     240
atcatatgac tttaagaccc tttaagggcg gcgagttaat tataagaccc ttaaagggcg     300
gtgagttaat tataagaccc tttaagtgcg gtgagttaat tataagaccc tttaagggcg     360
gtgagttaat gctaagaccc tttaagggtg acgagttaaa actatttttg agaataattg     420
aggactcgtg tgttttgtac agttcataga tagagtttgt gtgctaaaat gttttctgag     480
ttggacctga atcaggaggg agaggccctg acggactctt cggagtgtag gccttggggg     540
tcacccgatt tgagtgtttc tttaagccta tgttgatccc atatgattgg agcattctcg     600
taaaacactg tgatcctgac tggtctccct atgatattac ctagtgagag ttacttgact     660
tactagtgtg tggtttgtct tgtcatgtac tcctaggcgc ccgacgagat ttttcactga     720
catggtacca cattgcatat agacttgagt tttagcataa ctgttgcata cgcttgctaa     780
ttgtttatca tgaaattgat gtgttattat gtcttgatca gagtgtgtga ttcttgtata     840
ttgtgatgga tgattgaaag gtgtgattga ttgaaaagtg aattttgaat gacaaagtgg     900
tgaaataatg tgagctatgc taagtagatt gtatttggct actatatgtt atctcgtttc     960
tctctagtag ttaggaatgt gataactcac tctcggtttg ctggtatttg aatcctgtga    1020
tgatcctgaa ttttgtattc aaggagcgag atgactagat gaactgcttt aaggaatatt    1080
gtgctgaagg atgtcgggac acaatgctct gataggatgt gacattggat aataagtttt    1140
tatattaatt ttatcatgtt aatctatttt attttacctc actgatttaa caaaatattt    1200
ttataaattt gtgacggact tattttgagc cgaatatgtt tttaataagt tttaattgat    1260
aatagtgcag tggatgtgaa ccttttagcc atgtgaattt gttttccaat attttttatat    1320
attttattta tatatacata tatgtcgggg tagaggatgt cacatcttca ctccaaacat    1380
ctcattaata tcaatcatat tcttcttgat tatcatatct agccaccctt ttatctcatt    1440
tctttcacta ggtgtccaat aattttttag tgtctaccaa tccattttta tatatagata    1500
tatattgttg attatggtat tgatataaaa taattactat tgaaagtaac gattaatatt    1560
cattagaaat cgtgagcaca cttaaggtaa gtactctcct ttcattatga tttattttat    1620
atccaaagtc agaattcaaa ttctatatcg cttgcttatt aaacacaaac ttattttta    1680
catatatatt tcactgaaaa taaacataaa aatgacactt aataataatt gttttctttc    1740
tattttttga ataccaaaaa ctttgtttca tatgtaaagg gaaaggaat aatactatta     1800
agctacacca tgaaatcaaa caaaaattat cattgggaat gatataaaaa aatcaataaa    1860
tttatccaca tattataatt tatgatttca tacacaatag gataatagtt ttacactttc    1920
attgcaacag tatataatat gacatatttta tttctacgtt gtgtgcccac ttattcttta   1980
ataatagtag aagaggaaag ggaaattcaa tatttacttc ttcatttttcc cttttagccg   2040
```

```
ttcatcattt tttcaacttt gaaagttttt ttttgtcttt tttcaaaaga aattctcatt    2100
gtattaatac attgagaaaa gaagacaaag ataaaacaat gttaagttta agatgtgaaa    2160
aaccacgacc atttgagcct ctatatatag gtgtctcgta tgctcaaaca tgacaagcca    2220
gtgatagttg ctttcagata actgatagtt gtgtgcaatt atttgaattc aagaatgtct    2280
caacccgact cgttggtggc tgagattgag gtgaaaacct ctgctgatca cttttacgac    2340
accttgaagg gtaagaaaca gcatcgtatt catgatgttg cccctcatca tatccataag    2400
gtggaagttc atgaaggtga gtgggataaa tctggcaata tcaaggtgct acattcgct    2460 gatggtaagt taaacttaat aaacacaatt cacagctata tatcttctat tccatattgt    2520
tgttatgatt aagttatcat tgttattatt gttgttgaat attatgtagg ggacactgtt    2580
gagaccttaa aggagagagt tgattttgat gatgaaaaca agaagataac ctacaccata    2640
ttggagggtg tcatgttgaa gtactataag agctacaagg ttatcgttca tgttttacca    2700
aaaggtgatg agcacagcct tgtgaagtgg actttcttgt atgagaaggt ggatcacact    2760
gcccctgagc caaccaagta caaagatttg gtggttaaac tcaccaagaa cgtggaggct    2820
catcttgttg aggctcgtta aaatgatccc taagtggttc acgctaaata aagttgtgat    2880
gtgtgtggtg tgttgcatgt ggccccttgg ttaattatca gccattatgt ttgctttaaa    2940
ttgccgtgcg taatatgttg ttggttaact tgttaaaaat attggttctc aaccataagt    3000
tgtgtaatgt gttgttggtt tattcaaaat attggccggg gatcacaggg agggctacat    3060
gcctttgtat gtctgtgatt tgtaatcttc gaccagctat tgattaattg atgttaaggg    3120
ggatttatcc ttgtttgtct caaacatttt gccaaatact tttgataact agaaggtttg    3180
tggatagccg gttttcttc attgggaagc ttacaggcat gcattggcta aaaaccagaa    3240
gaaattaaat gtcaaaatgc ttccacaaaa gttgtttaat ttaaattaaa cacttgaata    3300
tgttttaatc cctgaaaaat ttacagatct tgcatttgat atttaataat ttctttctta    3360
acttttgatt cctgaaaaat tattttatat ttgattcttg                         3400
```

<210> SEQ ID NO 2
<211> LENGTH: 153
<212> TYPE: PRT
<213> ORGANISM: Glycine max

<400> SEQUENCE: 2

```
Met Ser Gln Pro Asp Ser Leu Val Ala Glu Ile Glu Val Lys Thr Ser
  1               5                  10                  15

Ala Asp His Phe Tyr Asp Thr Leu Lys Gly Lys Lys Gln His Arg Ile
             20                  25                  30

His Asp Val Ala Pro His His Ile His Lys Val Glu Val His Glu Gly
         35                  40                  45

Glu Trp Asp Lys Ser Gly Asn Ile Lys Val Leu Thr Phe Ala Asp Gly
     50                  55                  60

Asp Thr Val Glu Thr Leu Lys Glu Arg Val Asp Phe Asp Asp Glu Asn
 65                  70                  75                  80

Lys Lys Ile Thr Tyr Thr Ile Leu Glu Gly Val Met Leu Lys Tyr Tyr
                 85                  90                  95

Lys Ser Tyr Lys Val Ile Val His Val Leu Pro Lys Gly Asp Glu His
            100                 105                 110

Ser Leu Val Lys Trp Thr Phe Leu Tyr Glu Lys Val Asp His Thr Ala
        115                 120                 125
```

```
Pro Glu Pro Thr Lys Tyr Lys Asp Leu Val Val Lys Leu Thr Lys Asn
    130                 135                 140

Val Glu Ala His Leu Val Glu Ala Arg
145                 150

<210> SEQ ID NO 3
<211> LENGTH: 30
<212> TYPE: DNA
<213> ORGANISM: Glycine max

<400> SEQUENCE: 3 taagacccttt taagggcggt gagttaatta                                              30

<210> SEQ ID NO 4
<211> LENGTH: 144
<212> TYPE: PRT
<213> ORGANISM: Capsicum annuum

<400> SEQUENCE: 4

Met Gly Val Lys Gly Leu Ile Ala Ser Val Glu Val Cys Glu Gly Asn
  1               5                  10                  15

Leu Ile His Glu Leu Phe His Ile His Ala His His Val Pro Asn Ile
             20                  25                  30

Ser Pro Phe Ile Asn His Phe Glu Ile His Glu Gly Glu Thr Val Lys
         35                  40                  45

Val Gly Ser Val Val Ser Trp Ser Tyr Asn Glu Ala Gly Gln Lys Arg
     50                  55                  60

Tyr Met Lys Gln Leu Ile Glu Asp Ile Asp Pro Asp Met Lys Leu Ile
 65                  70                  75                  80

Arg Trp Lys Ala Ile Glu Gly Asp Val Leu Glu Ser Tyr Asn Ser Phe
                 85                  90                  95

Thr Ile Val Thr Ser Ser Glu His Glu Trp Thr Thr Trp Thr Ile Glu
                100                 105                 110

Tyr Glu Lys Lys Thr Glu Phe Thr Pro Glu Pro Leu Val Leu Leu Gly
            115                 120                 125

Leu Val Leu Asp Met Thr Lys Asp Ile Glu Ala His Leu Leu Lys Lys
        130                 135                 140

<210> SEQ ID NO 5
<211> LENGTH: 145
<212> TYPE: PRT
<213> ORGANISM: Nicotiana tabacum

<400> SEQUENCE: 5

Met Gly Leu Lys Gly Lys Leu Ile Ala Gln Ile Glu Met Lys Cys Ala
  1               5                  10                  15

Gly Asp Leu Leu His Glu His Phe Lys Ser Asn Pro His Gln Thr Ser
             20                  25                  30

Thr Met Ser Pro Asn Lys Ile Thr Asn Phe Thr Leu His Glu Phe Gln
         35                  40                  45

Leu Gly Ser Thr Gly Ser Val Val Ser Trp Lys Phe Val Leu Gly Gly
     50                  55                  60

Lys Glu Arg His Ala Lys Gln Val Leu His Ile Asp Asp Ala Lys Lys
 65                  70                  75                  80

Ser Ile Thr Phe Asn Phe Val Glu Gly Asp Met Asn Glu Leu Lys Ser
                 85                  90                  95

Met Thr Ala Thr Leu Thr Ala Glu Gly Asn Trp Met Thr Trp Thr Phe
                100                 105                 110
```

-continued

Val Tyr Glu Lys Leu Asn Glu Asn Ile Pro Glu Pro Leu Asp Ile Phe
        115                 120                 125

Glu Leu Ala Ile Cys Leu Leu Lys Asp Leu Pro His His Val Gly
    130                 135                 140

Lys
145

<210> SEQ ID NO 6
<211> LENGTH: 149
<212> TYPE: PRT
<213> ORGANISM: Cucumis melo

<400> SEQUENCE: 6

Met Ser Leu Ile Gly Lys Leu Val Ser Glu Leu Glu Ile Asn Ala Ala
1               5                   10                  15

Ala Glu Lys Phe Tyr Glu Ile Phe Lys Asp Gln Cys Phe Gln Val Pro
            20                  25                  30

Asn Ile Thr Pro Arg Cys Ile Gln Gln Val Glu Ile His Gly Thr Asn
        35                  40                  45

Trp Asp Gly His Gly His Ser Ile Lys Ser Trp Tyr Tyr Thr Ile Asp
    50                  55                  60

Gly Lys Ala Glu Val Phe Lys Gly Arg Val Glu Phe His Asp Asp Lys
65                  70                  75                  80

Leu Leu Ile Val Leu Asp Gly Val Gly Gly Asp Val Phe Lys Asn Tyr
                85                  90                  95

Lys Ser Phe Lys Pro Ala Tyr Gln Phe Val Pro Lys Asp Arg Asn His
            100                 105                 110

Cys Gln Ala Ile Leu Ser Ile Glu Tyr Glu Lys Leu His His Gly Ser
        115                 120                 125

Pro Asp Pro His Lys Ile Asp Leu Met Ile Gly Ile Thr Asn Asp Ile
    130                 135                 140

Gly Ser His Ile Lys
145

<210> SEQ ID NO 7
<211> LENGTH: 158
<212> TYPE: PRT
<213> ORGANISM: Papaver somniferum

<400> SEQUENCE: 7

Met Ala Glu His His His Thr Ile Ser Gly Leu Val Gly Lys Leu Val
1               5                   10                  15

Thr Glu Leu Glu Val Asn Cys Asn Ala Asp Glu Tyr Tyr Lys Ile Phe
            20                  25                  30

Lys His His Glu Asp Leu Pro Asn Ala Ile Pro His Ile Tyr Arg Gly
        35                  40                  45

Val Lys Ala Val Glu Gly Asp Arg Ile Thr Ser Gly Phe Ile Lys Glu
    50                  55                  60

Trp His Tyr Ile Ile Glu Gly Lys Pro Leu Thr Cys Lys Glu Arg Thr
65                  70                  75                  80

Thr Tyr Glu Asp Glu Ala Arg Thr Ile His His Ser Thr Val Glu Gly
                85                  90                  95

Val Leu Leu Asp Asp Tyr Lys Lys Phe Asp Ala Thr Leu Val Asn Pro
            100                 105                 110

Lys Ala Asp Gly His Gly Ser Ile Val Thr Trp Ile Val Glu Tyr Glu
        115                 120                 125

Lys Ile Asn Glu Asp Ser Pro Val Pro Ile Ser Tyr Leu Thr Phe His
       130                 135                 140

Lys Ile Ile Glu Asp Leu Asn Thr Tyr Leu Cys Ala Ser Asp
145                 150                 155

<210> SEQ ID NO 8
<211> LENGTH: 36
<212> TYPE: DNA
<213> ORGANISM: Artificial Sequence
<220> FEATURE:
<223> OTHER INFORMATION: Description of Artificial Sequence:
      oligonucleotide useful as a primer.

<400> SEQUENCE: 8
cccaagcttg ggcgagttta atcacaagca caacga                                36

<210> SEQ ID NO 9
<211> LENGTH: 33
<212> TYPE: DNA
<213> ORGANISM: Artificial Sequence
<220> FEATURE:
<223> OTHER INFORMATION: Description of Artificial Sequence:
      oligonucleotide useful as a primer.

<400> SEQUENCE: 9
cccaagcttg ggagcattct cgtaaaacac tgt                                   33

<210> SEQ ID NO 10
<211> LENGTH: 34
<212> TYPE: DNA
<213> ORGANISM: Artificial Sequence
<220> FEATURE:
<223> OTHER INFORMATION: Description of Artificial Sequence:
      oligonucleotide useful as a primer.

<400> SEQUENCE: 10
cccaagcttg ggctagatga actgctttaa ggaa                                  34

<210> SEQ ID NO 11
<211> LENGTH: 33
<212> TYPE: DNA
<213> ORGANISM: Artificial Sequence
<220> FEATURE:
<223> OTHER INFORMATION: Description of Artificial Sequence:
      oligonucleotide useful as a primer.

<400> SEQUENCE: 11
cccaagcttg ggccaaagtc agaattcaaa ttc                                   33

<210> SEQ ID NO 12
<211> LENGTH: 34
<212> TYPE: DNA
<213> ORGANISM: Artificial Sequence
<220> FEATURE:
<223> OTHER INFORMATION: Description of Artificial Sequence:
      oligonucleotide useful as a primer.

<400> SEQUENCE: 12
cgcggatccg cgcatcttga attctgactt tgga                                  34

<210> SEQ ID NO 13
<211> LENGTH: 31
<212> TYPE: DNA
<213> ORGANISM: Artificial Sequence
<220> FEATURE:
<223> OTHER INFORMATION: Description of Artificial Sequence:

oligonucleotide useful as a primer.

<400> SEQUENCE: 13
cgcggatccg cgcttgaatt ctgactttgg a                                    31

<210> SEQ ID NO 14
<211> LENGTH: 37
<212> TYPE: DNA
<213> ORGANISM: Artificial Sequence
<220> FEATURE:
<223> OTHER INFORMATION: Description of Artificial Sequence:
      oligonucleotide useful as a primer.

<400> SEQUENCE: 14
cgcggatccg cgcattcttg aattcaaata attgcac                              37

<210> SEQ ID NO 15
<211> LENGTH: 34
<212> TYPE: DNA
<213> ORGANISM: Artificial Sequence
<220> FEATURE:
<223> OTHER INFORMATION: Description of Artificial Sequence:
      oligonucleotide useful as a primer.

<400> SEQUENCE: 15
cgcggatccg cgtcttgaat tcaaataatt gcac                                 34

<210> SEQ ID NO 16
<211> LENGTH: 29
<212> TYPE: DNA
<213> ORGANISM: Artificial Sequence
<220> FEATURE:
<223> OTHER INFORMATION: Description of Artificial Sequence:
      oligonucleotide useful as a primer.

<400> SEQUENCE: 16
tacgtaatgg taagttaaac ttaataaac                                       29

<210> SEQ ID NO 17
<211> LENGTH: 28
<212> TYPE: DNA
<213> ORGANISM: Artificial Sequence
<220> FEATURE:
<223> OTHER INFORMATION: Description of Artificial Sequence:
      oligonucleotide useful as a primer.

<400> SEQUENCE: 17
tacgtatgtc ccctacataa tattcaac                                        28

<210> SEQ ID NO 18
<211> LENGTH: 32
<212> TYPE: DNA
<213> ORGANISM: Artificial Sequence
<220> FEATURE:
<223> OTHER INFORMATION: Description of Artificial Sequence:
      oligonucleotide useful as a primer.

<400> SEQUENCE: 18
gagctctaaa atgatcccta agtggttcac gc                                   32

<210> SEQ ID NO 19
<211> LENGTH: 31
<212> TYPE: DNA
<213> ORGANISM: Artificial Sequence
<220> FEATURE:
<223> OTHER INFORMATION: Description of Artificial Sequence:
      oligonucleotide useful as a primer.

-continued

```
<400> SEQUENCE: 19
ggaattccga caaacaagga taaatccccc t                                    31
```

SOYBEAN PROMOTER EXPRESSED PREFERENTIALLY IN PODS

CROSS REFERENCE TO RELATED APPLICATIONS

This application claims priority from U.S. Provisional Application No. 60/160,720, filed Oct. 20, 1999.

ACKNOWLEDGMENT OF FEDERAL RESEARCH SUPPORT

Not Applicable

BACKGROUND OF THE INVENTION

The field of this invention is the area of molecular biology, in particular, as related to tissue specific promoters of plants, and more particularly, to promoters which selectively direct expression of genetic information in the developing seedpod and certain other tissues of a legume or other plant.

There is a longfelt need in the art for expression control sequences which mediate tissue specific and/or developmentally regulated expression of nucleotide sequences of interest in plants. The present invention fills this need.

SUMMARY OF THE INVENTION

The present invention provides transcriptional regulatory sequences which mediate tissue specific and developmental stage specific expression of nucleotide sequences placed under the control of those transcriptional regulatory sequences, The tissue specificity of the transcription regulatory sequences of the present invention is such that expression occurs preferentially in the developing seedpod of a plant, especially of a leguminous plant, for example, soybean, green bean, or pea. The Msg transcription regulatory sequences also direct expression in guard cells of stem, in roots, shoots, node cells and flowers. The sequences of the present invention function in monocots or dicots. As specifically exemplified herein, the developing seedpod-specific promoter of the gene termed Msg herein, is from the genome of *Glycine max*. The transcriptional regulatory sequences of the present invention can include sequences which direct the initiation of transcription, for example the entire untranslated region, e.g., nucleotides −2260 to −1 of Table 1, relative to the translation start site, or −2260 to about −650 in the absence of other promoter sequences, or the sequences can be positioned upstream of and in the same orientation as a truncated promoter region (a truncated promoter region desirably includes a TATA region, and optionally at least one CAAT element). Chimeric genes of the present invention include transcription regulatory sequences which direct tissue-specific and developmental stage specific expression of downstream nucleotide sequences, primarily in developing and maturing seedpods, but not in developing seeds. The sequence downstream of the transcription regulatory element of the present invention can be any of a number of sequences including but not limited to a pathogenesis-related protein, a plant defense protein, lectins with specific binding activities, an antibacterial protein of a plant or animal, an insect-resistance gene such as a naturally occurring or a *Bacillus thuringiensis* insecticidal protein expressible in plants or a chitinase or a fungal resistance protein. Alternatively, the sequence to be expressed in the specifically regulated manner of the present invention can be a regulatory nucleic acid sequence whose expression is desired in the seedpod or guard cells in stem, roots, shoots, node cells and flowers, and the 3'UTR directs expression in the filaments of stamens.

The transcription regulatory sequences of the present invention can be isolated, using the specifically exemplified sequences as hybridization probes or to generate primers for polymerase chain reaction (PCR) amplification, from a legume, including but not limited to, soybean, green bean, other beans, pea, alfalfa, clover, among others, such as those plants which have dehiscent (dry) fruit including the Brassicaceae (canola, cabbage, mustard, broccoli, etc.), some members of the Solanaceae (e.g., tobacco), the Linaceae (e.g., flax and linseed), the Papaveraceae, and the horticultural species of the Ranunculaceae. Certain members of the Curcurbitaceae family, such as muskmelons and cucumbers, are also improved in pathogen resistance and/or drought resistance by expression of the exemplified Msg gene or by introduction of another pathogen resistance protein expressed under the control of the Msg transcription regulatory sequences. The nucleotide sequence of a specifically exemplified soybean pod-specific transcription regulatory region (of the Msg gene), including full promoter, is given in Table 1 herein. Shorter sequences can be derived from the exemplified sequence, where the shorter sequences are effective to regulate the transcriptional expression of a nucleotide sequence under their control. Specifically exemplified shorter sequences which retain the ability to regulate transcriptional expression of a downstream nucleotide sequence include those sequences of Table 1 and having limits as set forth in FIG. 6. It is understood that sequences in the region of about −2260 to about −650, or about −2274 to −1, or about −2274 to about −650, relative to the translation site, direct the initiation of transcription in the desired tissue-specific and/or developmentally regulated manner.

The present invention further provides plant transformation vectors which comprise the transcription regulatory sequences of the present invention together with operably linked downstream sequences to be expressed in a plant in a tissue specific and developmental pattern specific fashion. The vectors can be introduced into plant cells or tissue by any methods known to art, including but not limited to, Agrobacterium-mediated transformation, electroporation, microinjection and microprojectile bombardment. Regeneration of plants from transformed cells and tissue is well known to the art.

Also within the scope of the present invention are plant cells, plant tissue, transgenic plants, pod cells, seeds, etc., which contain a heterologous nucleotide sequence expressed under the regulatory control of the pod specific transcription regulatory sequences described herein.

Additional objects of the present invention include the production of transgenic plant cells, tissue and plants in which a nucleotide sequence of interest is operably linked to transcription control sequences which mediate expression of the sequence of interest in a tissue specific fashion, preferentially in the seedpod (but not in the seed) of such a transgenic plant. Additional sites of expression of the Msg-regulated transcript include, but are not limited to, guard cells of stem, cells in nodes, shoots, roots and flowers, but not seeds.

The method of the present invention comprises the step of introducing a recombinant DNA construct comprising an Msg-regulated nucleotide sequence into a plant cell or into plant tissue, such that the construct becomes stably incorporated within the genome of said plant cell. In the present context, the construct can simply be a sequence operably linked to the transcription regulatory sequences of the present invention, or the construct can further include a selective marker which readily allows the skilled artisan to determine incorporation of the construct, and the construct can comprise vector sequences which allow amplification of the construct in a host cell other than a plant cell (e.g., the vector sequences can be a plasmid sequences). Transgenic plants are regenerated from the stably transformed plant cells or tissue according to art-known techniques.

BRIEF DESCRIPTION OF THE DRAWINGS

In FIG. 1B, the film is overexposed to illustrate the weak expression that is present in roots, nodes, stems, shoot tips and flowers as compared to the high expression in pods.

FIG. 3: The nucleotide sequence (SEQ ID NO:1) of Msg and flanking regions. The primers used to obtain the PCR fragments for the promoter analysis are indicated by an arrow, with the overhang indicated by the name of the restriction site. Restriction sites are underlined and the splicing sites of the intron are marked by vertical arrowheads. The putative TATA box, start, stop and polyadenylation signals are boxed. The original cDNA sequence (VS-107) is indicated by a dashed overline, starting and ending with arrows. The protein sequence (SEQ ID NO:2) is given below the coding nucleotide sequence. At −1871 to −2026 bp, five highly conserved repeats are located (marked with thin lines and arrows). DNA sequence numbering is negative upstream of the translation start sequence, and positive numbers begin at the start of the coding sequence.

FIG. 4: Sequence alignment of the published proteins belonging to the major latex protein homolog family. The MAP, Multiple Sequence Alignment function at BCM Search Launcher was used for the alignment. Only those amino acids that perfectly match with Msg have been boxed. The Msg (*Glycine max*) is marked in bold. *Capsicum annuum* (Sn-1), GenBank Accession No. X79230, SEQ ID NO:4; *Nicotiana tabacum*, (FB74), GenBank Accession No. S44872, SEQ ID NO:5; *Glycine max* (Msg), GenBank Accession No. AJ239127, SEQ ID NO:2; *Cucumis melo* (MEL7), GenBank Accession No. Z70522, SEQ ID NO:6; *Papaver somniferum* (MLP 22), GenBank Accession No. S28427, SEQ ID NO:7.

In FIG. 6A, the promoter of Msg was successively 5'-deleted as indicated in the G305atg-N353 constructs and the resulting regions were fused to the uidA (GUS) reporter gene. In FIG. 6B, each of the A92atg-F219 constructs also lack 635 bp adjacent to the start codon of the Msg gene that contains the TATA box. [Note: Because the primers used to amplify the M347atg and N353 constructs contains 17 bases of Msg sequence, the total lengths of the M347atg and N353 constructs are 655 and 652 bp, respectively; whereas, the exact length of the deletion in the A92atg-F219 constructs is 635 bp. These exact sizes are shown in the figure., however, for simplicity throughout the paper, we have referred to the promixal region as 650 base pairs.] The PCR primers indicated in the figure were custom made with restriction enzyme overhangs (Hin dIII and Bam HI) to facilitate cloning of the fourteen different promoter PCR fragments into the promoterless binary vector pBI101. For each construct there are two versions; one contains the start codon (atg) incorporated into the primer that amplifies the Msg-promoter fragment and the other contains the start codon from the uidA gene. The "atg" in the vector name designates the construct in which the atg derives from the primer used to amplify the Msg-promoter. The "atg" constructs encode 9 extra amino acids from the polylinker region fused to GUS whereas the other constructs contain these 27 bases as part of the non-translated region.

FIGS. 7A–7F show stable expression of GUS in Arabidopsis under control of Msg-promoter deletions. FIG. 7A: A transformant (t) and a control non-transformant plant (c). (×8) FIG. 7B: A group of strongly expressing cells are situated in the node by the base of cauline leaves and pedicels. The guard cells of the upper stem and pedicels are also GUS positive. (×32) FIG. 7C: Guard cells of a silique expressing GUS. (×200) FIG. 7D: GUS expression in nectaries at the base of the flower, petals, sepals, and short style (arrow) of the pistil/premature silique. (×20) FIG. 7E: GUS expression in nectary lobes and adjacent cells of the nectary at the base of the flower or silique are expressing GUS. (×32) FIG. 7F: Siliques of T1 plants transformed with (from left to right): G305atg (2.26 kb), J312 (1.68 kb), K340atg (1.22 kb). FIGS. 7G–7I show transient GUS expression in pods of soybean (*Glycine max*), and green bean (*Phaseolus vulgaris*), following particle bombardment. (×5) FIG. 7G: Soybean pod bombarded with pBMGL318 (1.22 kb). FIG. 7H: soybean pod bombarded with control 35S-GUS construct. FIG. 7I: green bean pod bombarded with pBMGB103 (1.62 kb, and lacking the proximal 635 bp).

FIG. 9A: Schematic of the genomic Msg region. FIG. 9B: The dark boxes represent the Msg upstream regions in the 5' deletion constructs. FIG. 9C: 5' deletion constructs lacking the 650 proximal base pairs. FIG. 9D: Different combinations of 5' promoter, 3'UTR and intron from the Msg-gene. FIG. 9E: A promoterless uidA with the Msg terminator (3'UTR), the promoterless pBI101 and the constitutive pBI121 were used as controls. Nomenclature: I, intron; Tm. Msg terminator (3'UTR); Tn, nopaline synthetase terminator; CaMV35S, cauliflower mosaic virus promoter for 35S fragment; uidA, beta-glucuronidase (GUS) reporter gene.

DETAILED DESCRIPTION OF THE INVENTION

Figure 1A:
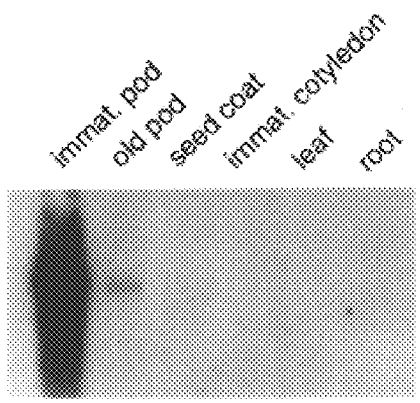
FIGS. 1A–1B: Preferential expression of cDNA clone VS-107 in developing soybean pods. Total RNA, 10 μg per lane, from the indicated tissues and stages of development were hybridized with the labeled insert of cDNA clone VS-107 from the pod cDNA library.

Abbreviations used herein for amino acids are standard in the art: X or Xaa represents an amino acid residue that has not yet been identified but may be any amino acid residue including but not limited to phosphorylated tyrosine, threonine or serine, as well as cysteine or a glycosylated amino acid residue. The abbreviations for amino acid residues as used herein are as follows: A, Ala, alanine; V, Val, valine; L, Leu, leucine; I, Ile, isoleucine; P, Pro, proline; F, Phe, phenylalanine; W, Trp, tryptophan; M, Met, methionine; G, Gly, glycine; S, Ser, serine; T, Thr, threonine; C, Cys, cysteine; Y, Tyr, tyrosine; N, Asn, asparagine; Q, Gin, glutamine; D, Asp, aspartic acid; E, Glu, glutamic acid; K, Lys, lysine; R, Arg, arginine; and H, His, histidine. Abbreviations for nucleotides are according to IUPAC nomenclature.

Combinatorial regulation is the result of trans-acting factors interacting with the specific set of cis-regions (boxes or elements) in a promoter, leading to tissue-specific gene expression [Singh, K. B. (1998) *Plant Physiol* 118:1111–1120]. The trans-acting factors themselves may be expressed tissue-specifically or constitutively. Many previously reported promoters are shown to have elements that control the levels of gene expression (quantitative regions, enhancers) at distal 5'-sites and tissue-specific regions proximal to the TATA box [Stougard et al. (1987) *EMBO J.* 6:3565–3569; Bustos et al. *EMBO J.* 10:1469–1479; Zhao et al. (1994) *Plant Mol. Biol.* 25:429–436; Hamilton et al. (1998) *Plant Mol. Biol.* 38:663–669; Ruiz-Rivero and Prat (1998) *Plant Mol. Biol.* 36:639–648]. The TATA-box is the binding site for the TBP (TATA-box binding protein) which is part of the transcription-initiation complex. In a recent report it was shown that in a mammalian system, naturally occurring transcription-initiation complexes that lack TBP or TBP-like proteins could initiate transcription from both TATA containing as well as TATA-lacking promoters [Wieczorek et al. (1998) *Nature* 393:187–191]. We report herein the discovery of a novel soybean gene, the Msg-gene, whose 5'-flanking promoter has multiple tissue-specific cis-regions that extend to over 2 kb upstream of the start site of the Msg coding sequence. Even more unusual is that the TATA box and 650 bases of proximal 5'-sequence of this promoter can be eliminated without affecting the basic tissue-specific expression patterns of the reporter gene.

This unusual gene was found in a search for pod specific promoters that can be used to direct expression of anti-fungal genes in the pod, especially of legumes. The pod is responsible for protecting the developing seeds from pathogens, and especially fungal pathogens, which can attack soybean or other leguminous pods, leading to decreased seed yield and quality. Many seedborne fungi will also kill the next generation of seedlings. Pod and stem blight (Diaporthe/Phomopsis) [Kulik, M. (1984) *Mycologia* 76:274–291], pod and seed decay (Alternaria) and anthracnose (Glomerella) [Schneider et al. (1974) *Phytopathology* 64:154–155] are some examples of fungal pathogens on soybean. By expressing anti-fungal proteins in the pod but not in the seed itself, the fungus is inhibited, and the risk is small for carry over of foreign substances (i.e. anti-fungal proteins) in the seed product.

Figure 1B:
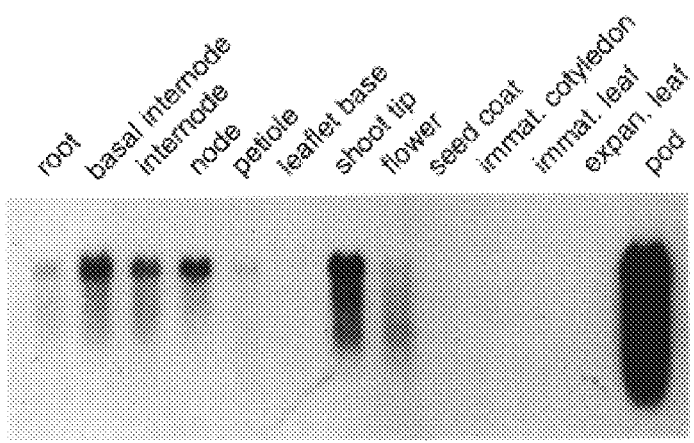
Figure 1C:
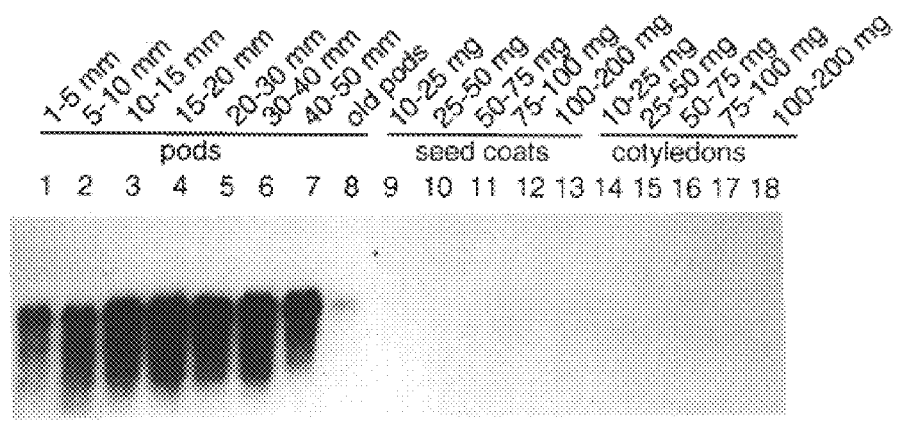
FIG. 1C: Total RNA from the different stages of development of pods (lanes 1–8, pod length indicated), seed coats (lanes 9–13, from seed of the indicated fresh weight range) and cotyledons (lanes 14–18, from seed of the indicated fresh weight) was hybridized to cDNA clone VS-107.

We constructed a lambda cDNA library of soybean pod mRNA and isolated 160 random lambda clones. The insert from each clone was labeled and used to examine its expression pattern by hybridization to total RNA extracted from soybean roots, stems, leaves, seed coats, cotyledons and pods. FIG. 1A shows a Northern blot probed with the insert from the random cDNA clone VS-107. This clone is highly expressed in the developing pods while virtually no expression can be detected in the other tissues assayed. Sometimes a very weak expression is observed in roots, nodes and stem as seen in the overexposed Northern blot in FIG. 1B. In FIG. 1C, the pod specificity is demonstrated by hybridization of VS-i107 to RNA extracted from pods (lanes 1–8), cotyledons (lanes 14–18) and seed coats (lanes 9–13) at different stages of development. No expression of VS-107 can be detected at any time or stage of development in the seed coats or cotyledons. In the pods however, the expression is high at all stages of pod expansion up to full length of 4 to 5 cm. Expression of VS-107 mRNA declines in older pods as the seeds reach full maturity before dehydration.

Figure 2:
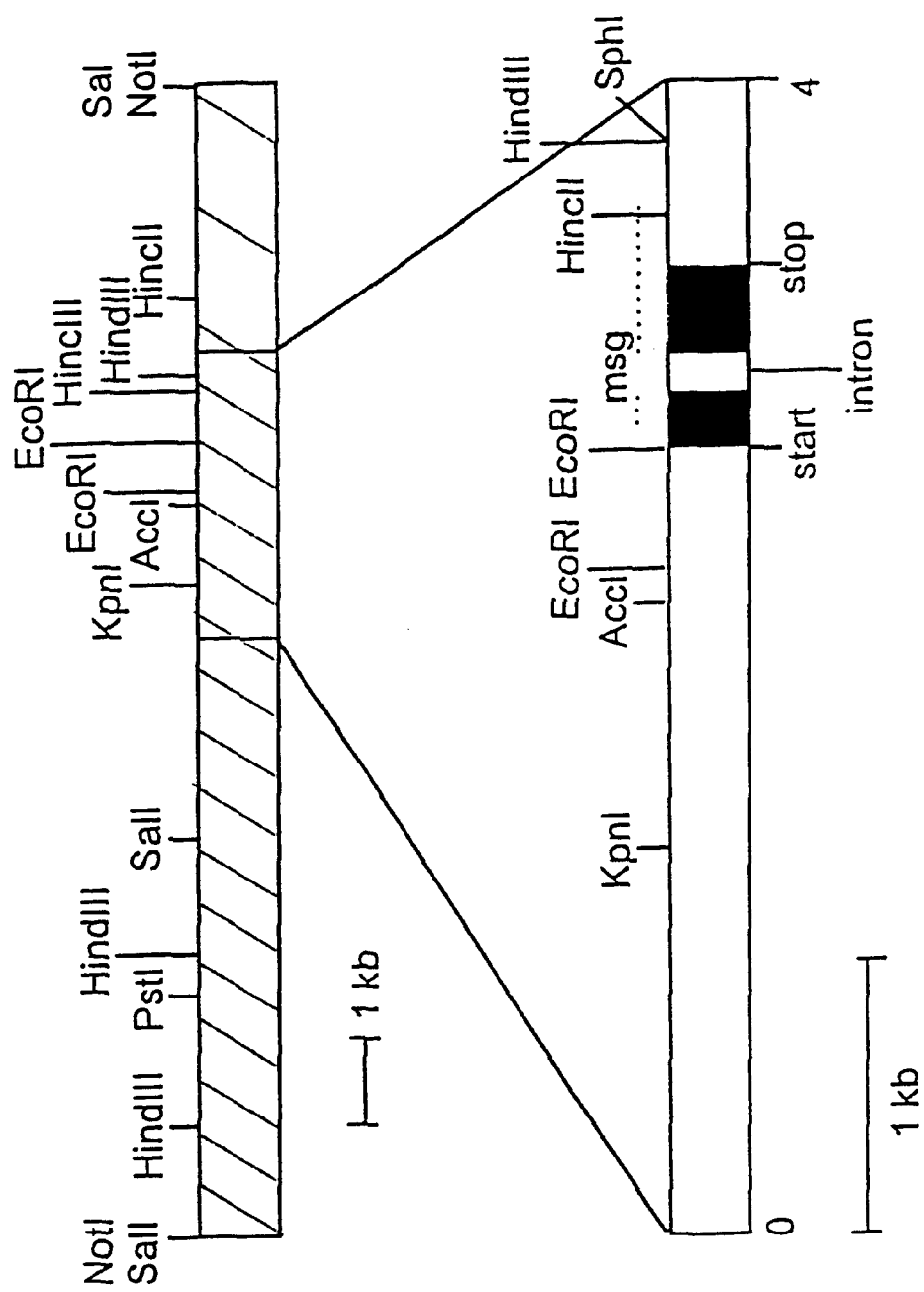
FIG. 2: Map of the 16 kb Msg genomic fragment representing the pod specific cDNA clone VS-107. The enlarged segment represents the 4 kb of the Msgb clone that have been sequenced and the dark boxes represents the two exons of the Msg-gene, interrupted by a small intron. The sequence of the original cDNA clone (VS-107) is marked with a dashed line.

Using the VS-107 cDNA clone as a probe, a soybean genomic lambda library was screened. Out of about 500,000 genomic lambda clones screened, two positive clones were isolated and designated Msga and Msgb. Restriction mapping showed that the 16 kb Msgb insert contained more flanking DNA than the 13 kb Msga clone and was therefore chosen for further investigation. FIG. 2 shows a schematic view of the lambda Msgb insert and the 4 kb that have been sequenced, containing the coding region of Msg gene that corresponds to the VS-107 cDNA.

FIG. 3 shows the sequence of Msg and about 2.8 kb of the 5'-flanking region. The coding region of the gene is 459 bp long and it is interrupted by an intron of 105 bp at position +190 to +295 in the figure. About −2 kb (−1871 to −2021 bp) from the start of translation, there are five conserved direct repeats of 30 bp each in a row with a consensus sequence of 5'-TAAGACCCTTTAAGGGCGGTGAGTTAATTA-3' (SEQ ID NO:3). These repeats have the potential to form hairpin structures and/or act as binding sites interacting with the regulation of the gene. The putative TATA-box (TATATATA) is positioned at −89 to −96 from the translational start and the poly-A signal (AATAAA) at +593 to +598, 25 bp downstream of the stop codon (TAA). When aligning the cDNA sequence to the genomic sequence, the 300 bp long 3' untranslated region is evident. The original cDNA (VS-107) was not full length, it begins at position +85, and the intron was spliced, following the GT-AG rule. Full-length cDNAs have been isolated from the original cDNA library using the VS-107 as a probe. The Msg gene, when translated, yields a 17.7 kDa protein (153 aa) with a predicted pI of 6.25.

Database analysis of the coding sequence indicates that the gene belongs to a family of fruit and flower specific genes, the major latex protein homologs. These are so far reported in opium poppy (*Papaver somniferum*) [Nessler et al. (1990) *Planta* 180:487–491]; tobacco (*Nicotiana tabacum*) [Meeks-Wagner et al. (1989) *Plant Cell* 1:25–35; Neale et al. (1990) *Plant Cell* 2:673–684]; bell pepper (*Capsicum annuum*) [Pozueta-Romero et al. (1995) *Plant Mol. Biol.* 28:1011–1025]; musk melon (*Cucumis melo*) [Aggelis et al. (1997) *Plant Mol. Biol.* 33:313–322]; and wild strawberry (*Fragaria vesca*) [Nam et al. (1999) *Plant Mol Biol.* 39:629–636]. There are also latex protein-like sequences in the databases for *Arabidopsis thaliana*, rape seed (*Brassica napus*), raspberry (*Rubus idaeus*) and common ice plant (*Mesembryanthemum crystallinum*). The function/s of the Msg protein and its family members are unknown, but they are all expressed in fruits and/or related organs such as flower parts, and, in general, they are of low copy number. They are between 16.8–18.1 kDa in size, and pI's range from 5.5–6.7. These sequences also show significant homology to pathogenesis related plant proteins (PR-proteins) such as ribonuclease of ginseng [Moiseyev et al. (1997) *FEBS Lett*. 407:207–210] and the parsley PR1 protein [Rushton et al. (1996) *EMBO J*. 15:5690–5700] and to the related allergens such as Api g I of celery, [Breiteneder et al. (1995) *Eur. J. Biochem*. 233:484–489] and especially to the major tree pollen allergen proteins e.g. Cor a I of hazel and Car b I of hornbeam [Breiteneder et al. (1993) *Eur. J. Biochem*. 212:355–362; Larsen et al. (1992) *Mol. Immunol*. 29:703–711, respectively]. Without wishing to be bound by any particular theory, it is believed the Msg protein improves survival and reproduction of podded seeds by inhibiting pathogen and/or pest attack and by improving desiccation resistance.

FIG. 4 presents an alignment of the gene products of the published major latex homologs. In the figure, only those amino acid residues that are identical matches to the soybean Msg have been boxed. Some regions are highly conserved, for example a glycine at position 62 in the figure, a lysine at position 81, an isoleucine at 94, a glutamic acid and a glycine at 100–101, a tyrosine, a lysine and a serine at 107–108, a tyrosine, a glutamic acid and a lysine at 132–134, proline-glutamic acid-proline at 140–142 and finally a histidine at 159. The melon MEL7 is 31.6% identical to the Msg protein, the poppy MLP22 is 29.6% identical, the tobacco FB7-4 protein 29.4% identical, and the bell pepper Sn-1 protein is 28.6% identical to the Msg protein. In general, these proteins have about 30% overall identity to each other and as a group they show about 25% identity to the IPRs [Osmark et al. (1998) *Plant Mol. Biol*. 38:1243–1246].

The 5'-flanking region of the Msg gene is very A/T-rich (68% overall in the region investigated) and has a region at −711 to −767 bp that shows high homology (70% identity) with a promoter region from a soybean heat shock protein [Schöffl et al. (1984) *EMBO J*. 3:2491–2497].

Figure 5:
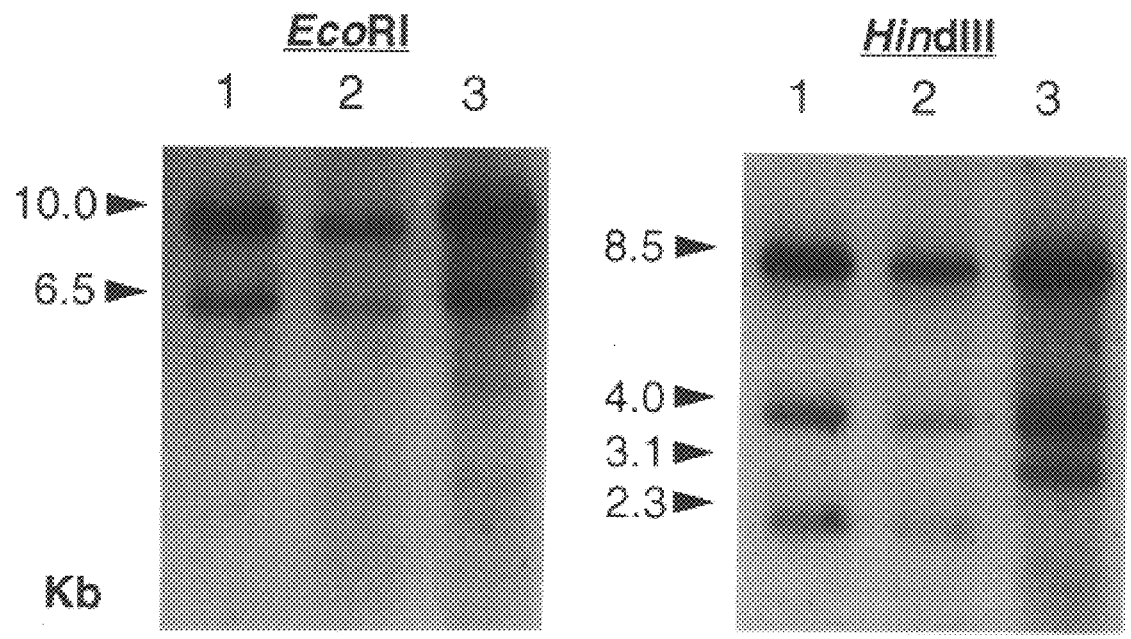
FIG. 5: Genomic DNA blots indicate that there are at least two Msg genes in soybean. Genomic DNA (10 g) was digested with Eco RI or Hin dIII, electrophoresed, and probed with the cDNA clone VS-107. Lane 1 is the cultivar Richland, lane 2 is T157, and lane 3 is the cultivar Williams. The cultivar Clark has the same polymorphism as Williams (not shown).

FIG. 5 shows the restriction fragment patterns of genomic DNA when hybridized to the VS-107 cDNA clone. There are possibly one or two additional copies of genes related to Msg based on both the Eco RI and Hin dIII restriction patterns. Two Eco RI fragments of 10.0 kb and 6.5 kb are found although there are no Eco RI sites internal to the probe (the VS-107 cDNA-clone). Three bands are detected with Hin dIII digestion, the longest of which is about 8.5 kb. This fragment is consistent with a Hin dIII—Hin dIII fragment of the Msgb map (FIG. 2). The other two fragments in the Hin dIII genomic blot are about 4 and 2.3 kb or 4 and 3.1 kb for the Williams variety (lane 3). Each of these two fragments could represent additional copies of genes related to Msg. Alternatively, they might represent one copy containing a Hin dIII polymorphism that interrupts the coding region of that gene. The two smaller bands are also fainter than the 8.5 kb band, which could be due to sequence divergence with a second or third copy of the Msg sequence. FIG. 5 also shows that there is a polymorphism detected in one of the Hin dIII fragments in the cultivar Williams.

A gene homologous to Msg called Msg2(6C) was cloned by PCR using the Msg2690 and Msg3619 primers and genomic DNA from the soybean cv Williams as template. This fragment is 950 bp in size and includes the 5' and 3'UTRs, both exons and the intron. The coding region of Msg2(6C) is identical to Msg. In the Msg2(6C) intron a single base pair polymorphism (a G that corresponds to an A in Msg) is present that yields a Hin dIII site. In addition there is an extra T four bases further downstream that is not present in the Msg intron. In the 3'UTR there are two instances of a T in Msg corresponding to a C in Msg2(6C).

Based on the cDNAs and the additional cloned Msg2(6C) there are at least two different homologues of Msg in the soybean genome. A homologue that is expressed in the root of soybeans, G08 (AC #AAD50376) is also reported in the database. Msg and G08 are about 30% identical at the amino acid level.

Figure 6:
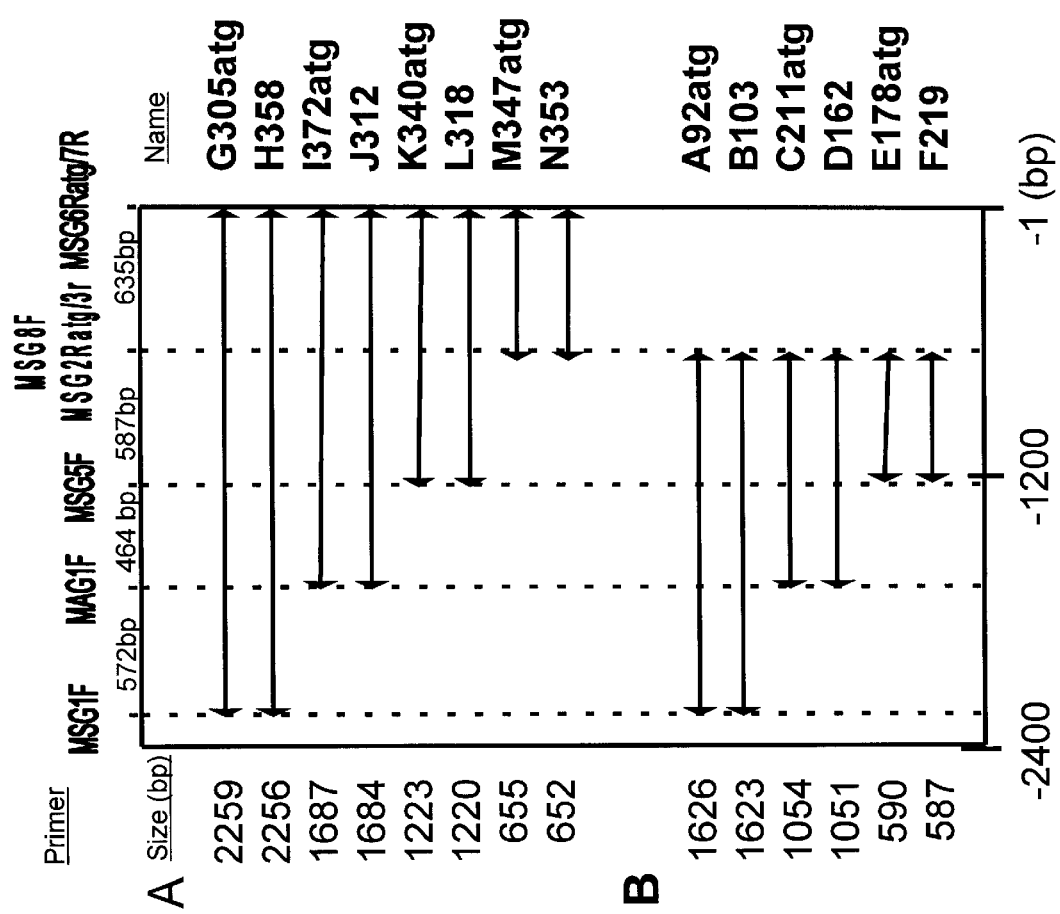
FIGS. 6A–6B: Deletion constructs of the Msg-promoter.

Fourteen PCR generated deletions of the Msg-promoter were fused to the uidA gene in the pBI101 binary vector [Bevan, M. W. (1984) *Nucleic Acids Research* 12:8711–8721; Jefferson et al. (1987) *EMBO J*. 6:3901–3907]. FIG. 3 shows the positions of the primers and FIG. 6 shows the names and sizes of the constructs. Series G305atg-N353 represents a conventional deletion series in which successively longer regions of the 5'-flanking promoter are eliminated as shown in FIG. 6A. Series A92atg-F219 represents the same three distal 5'-deletion fragments as G305atg-L318 except that the 650 bp proximal to the start codon of the Msg gene have also been deleted as shown in FIG. 6B. In essence, A92atg-F219 represent the deletion of the 650 bp Eco RI fragment of the promoter (FIG. 3) that contains the TATA box and all of the 5'-untranslated region of the Msg gene. Initially, this deletion was a mistake in that the close proximity of the Eco RI site to the start site of the gene lead to accidental loss of that fragment in subcloning of the promoter region.

The PCR primers were designed to anneal at 2.26, 1.68, 1.22 and 0.65 kb from the translational start codon of the gene. The reverse primer used to amplify the Msg-promoter was designed to either include or exclude a start codon in the overhang. The A92atg, C211atg and E178atg constructs contain an atg provided by the primer. The practical difference between the "atg-constructs" and the others is that in the "atg-constructs", 10 extra amino acid residues (9 without the methionine) from the polylinker cloning region will be fused to the GUS protein. In the B103, D162, and F219 constructs on the other hand, 30 extra base pairs will be part of the untranslated region. The inserts of all 14 constructs were confirmed by PCR and by Southern blot following Bam HI and Hin dIII restriction digests of plasmid preparations.

Figure 7A:
FIGS. 7A–7I: Transient and stable expression patterns of Msg-promoter:GUS fusions.
Figure 7B:
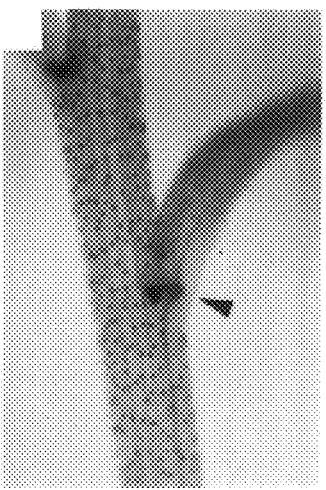
Figure 7C:
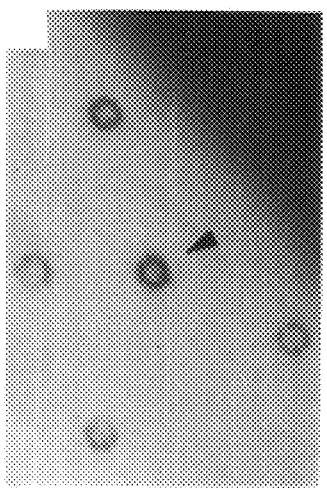
Figure 7D:
Figure 7E:
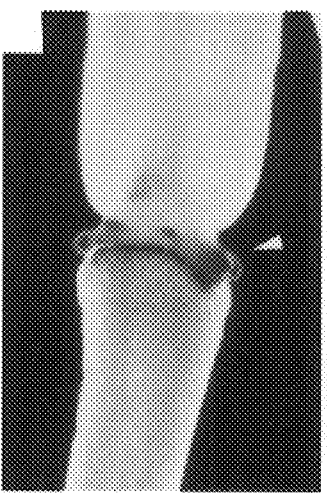
Figure 7F:
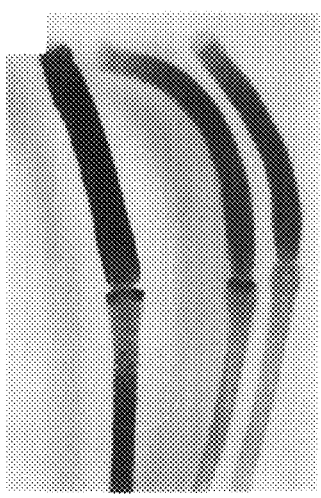

The 14 Msg-promoter constructs were transformed into *Agrobacterium tumefaciens* strain GV3101 (pMP90) [Koncz and Schell (1986) *Mol Gen. Genet*. 204:383–396], which were then used for vacuum infiltration or floral dipping mediated transformation [Bechtold et al. (1993) In: planta Agrobacterium Mediated Gene Transfer by Infiltration of Adult *Arabidopsis thaliana* Plants. C.R. Acad. Sci. Paris, Life Sci. 316:1194–1199; Clough and Bent (1998) *Plant J*. 16:735–743] of *Arabidopsis thaliana* ecotype Columbia. Bolting plants were subjected to vacuum infiltration of Agrobacterium and the seeds were harvested and selected on plates containing kanamycin. T1 transformants were transferred from the plates to soil and a histochemical GUS assay was performed on flowers, leaves, and siliques at different stages of development. Southern blots confirmed that all constructs have been successfully transformed into Arabidopsis. FIGS. 7A–F show GUS expression in Arabidopsis transformants. The longest construct (the G305atg, 2.26 kb) drives GUS expression in the flower (short style, sepals, sometimes stamens), the nectaries and in the guard cells of the silique and the pedicel and sometimes in hydatodes but not in the leaves. In general, fewer expressing cell types and less intense expression was correlated with successive deletion of the 5'-region as illustrated in FIG. 7F. In addition, developing siliques generally showed higher expression than mature siliques. The short style expressed GUS at early silique development but not in mature siliques.

The guard cells and nectaries also showed the highest expression during flowering and in the early stage of silique development. The T2 and T3 generations show a similar pattern of gene expression.

There was no major difference found between the expression pattern and the position of the ATG in the different constructs. Therefore, these have been grouped together in FIG. 8, which presents a graphical representation of the expression patterns found in the 14 constructs. The largest number of cell types that express GUS in Arabidopsis were obtained with the largest promoter fragments (2.26 kb, constructs G305atg and H358). In these cases, GUS is expressed in nodes, sepals, short style, nectaries, and in guard cells of the silique and the pedicel. Sometimes guard cells of the cauline leaves expressed GUS though no expression was ever observed in guard cells of mature leaves. Within the same raceme, GUS was sometimes present in some pedicels but not in others. Interestingly, if the 650 bp proximal to the start of translation is removed (constructs A92atg and B103), the expression in short style and sepals is generally weakened but is otherwise similar to that of the G305atg and H358 transformants.

When the 570 bp most distal to the translation start site are removed (C211atg, D162, I372atg and J312 constructs), expression is lost in the guard cells, sepals, short style and nectary lobes, and only nectary base cells and nodes show some expression. If another 460 bp are deleted, only nodes (E178atg and K340atg construct) and occasionally nectary base cells (L318 but not F219 construct) show expression.

All of the A92atg-F219 transformants, which lack the proximal 650 bp with the TATA box, show similar patterns as the corresponding 5'-deletion transformants (G305atg-L318), although with somewhat weaker levels of expression. Thus, the 650 bp proximal deletion that contains the TATA box does not seem to alter the tissue-specific expression pattern. The constructs that contain only the 650 bp proximal to the start site of the Msg gene are not expressed at all in Arabidopsis, although they are expressed transiently in soybean pods as are all of the constructs (see below). It is clear that the most distal 5'-sequences of the Msg-promoter are required for adding tissue-specific expression in Arabidopsis with or without the proximal 650 bp containing the TATA box.

The pBMGU1 and pBMGIU44 constructs both follow the pattern of pBMG305atg, that is they express in guard cells, nectaries, sepals, stamens, short style and nodes. The pBMMIU32 construct did not support detectable GUS activity. Curiously, for both pBMMU12 and pBMU2 there were transformants showing GUS expression in the filaments of the stamens. In the pBMMU12 transformed lines, GUS was weakly expressed internal to the nectary and in the ground tissue of the silique. The different expression patterns in the two different lines were observed in both the T1 and T2 generations. In addition to the expression in the flower, one pBMMU12 line lead to expression in the nodes. Because the constructs with the Msg3'UTR lead to GUS expression in additional tissues compared to the construct with the nos terminator, no quantitative GUS assays were performed.

To rule out background GUS staining in the plants due to potential bacterial activity, Agrobacterium carrying the pBMG305, pBMM347, pBMGU1, pBMGIU44, pBMMU12, XpBMMIU32, pBMU2, pBI101 and pBI121 constructs were assayed for GUS activity. As expected, none of the tested Agrobacteria carrying the Msg-intron constructs express GUS. The constructs with promoters but without the Msg intron expressed GUS. Surprisingly, the bacteria carrying the pBI101 and pBMU2 plasmids, both without a promoter directly 5' of uidA, expressed GUS. This could be due to a read through from the Pnos promoter that drives nptII, since it is in the same direction as and upstream of uidA. There is a nos-terminator but maybe the bacterium can ignore this. The pBI101 construct has never resulted in GUS expression in Arabidopsis.

Figure 7G:
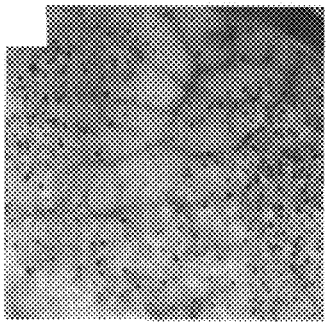
Figure 7H:
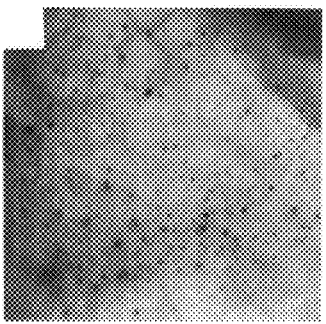
Figure 7I:
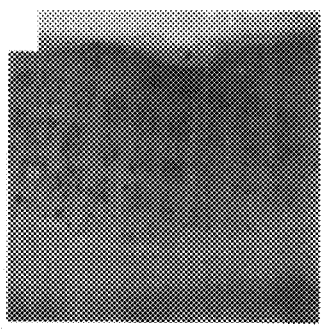

Particle bombardment [Klein et al. (1987) *Nature* 327:70–73; Finer et al. (1992) *Plant Cell Rep.* 11:323–328] of developing soybean and green bean pods were performed to test for transient expression of the constructs. All fourteen Msg-promoter:GUS-constructs, a CaMV35S:GUS positive control construct (pZA300) and the pBI101 promoterless negative control were precipitated on gold particles. Soybean and green bean pods were surface sterilized and the pods were shot on the inside surface after the seeds were removed. Two days after bombardment, a histochemical GUS assay was performed. (FIGS. 7G, 7H, 7I) illustrate the typical results. In soybean pods, visual examination indicates that the G305atg-N353 constructs express GUS stronger than the control CaMV35S:GUS construct. The A92atg-F219 constructs are almost as strong as the CaMV35S control for both soybean and green bean pods. No expression was seen when bombardment was done with the promoterless plasmid vector (pBI101).

Typically after bombardment of developing soybean pods, the sclerenchyma cells and inner epidermis cells in the seed cavity were transformed leading to the conclusion that the promoter is transiently active in both of these cell types. Similarly, in green bean pods the inner epidermis and the immediately underlying tissue in the seed cavity express GUS. The CaMV35S:GUS positive control construct also gave the same cell type pattern. Bombardment of soybean cotyledons, seed coats and leaves showed a maximum of 1–2 dots per bombardment, which could be due to contamination. Though transient expression of the Msg promoter is strong in the pods, it is not detected in the leaves and this result is consistent with the general pattern seen in RNA blots (FIG. 1).

To test that the transiently expressing tissue in soybean pods is sclerenchyma, soybean pods, bombarded and unbombarded, were stained for lignin with phloroglucinol. The inner epidermis, mesocarp parenchyma and outer epidermis did not stain red but the layers underlying the inner epidermis did. The carpellary bundles stained red as well (they contain lignified vascular tissue).

The Msg 3'UTR was amplified by PCR using primers designed with Sst I and Eco RI overhangs (Table 2). The digested fragment was cloned into the pBI101 plant transformation vector, replacing the nos terminator and resulting in the construct pBMU2. The M (650 bp) and G (2.26 kb) promoter fragments were then cloned upstream of uidA in pBMU2. The construct with the Msg 3'UTR and G is called pBMGU1 and with the 3'UTR and M is called pBMMU12. The PCR fragment of the intron was blunt end cut with Sna BI and cloned into the Sna BI site of uidA in pBMGU1 and pBMMU12, resulting in the vectors pBMGIU44 and pBMMIU32 respectively. FIGS. 8A–8E shows all the constructs with Msg intron and 3'UTR. The T-DNA region of pBMGIU44 is presented in FIG. 9.

The following is a series of vectors: pBMM347, pBMG305, pBMU2, pBMMU12, pBMGU1, pBMMIU9, pBMGIU44. In the vector name, the B means that it is derived from the pBI101 vector; the M is a cloner signature; the following (second) M is the 650 bp 5'Msg fragment or the following G is the 2.2 kb 5'Msg fragment; the I is the Msg intron; the U is the Msg3'untranslated region and the number is a clone identifier. The vectors pBI101 and pB121 are widely available the art.

The Msg intron eliminates bacterial GUS expression and the Msg 3'UTR leads to expression in the filaments. The pBMGU1 and pBMGIU44 constructs both follow the pattern of pBMG305atg, that is they express in guard cells, nectaries, sepals, stamens, short style and nodes. The pBMMIU32 construct did not .show any GUS activity. Curiously, for both pBMMU12 and pBMU2, there were transformants showing GUS expression in the filaments of the stamens. In the pBMMU12 transformed lines, GUS was weakly expressed internal to the nectary and in the ground tissue of the silique. The different expression patterns in the two different lines were observed in both the T1 and T2 generations. In addition to the expression in the flower, one pBMMU12 line lead to expression in the nodes. Since the constructs with the Msg 3'UTR lead to GUS expression in additional tissues compared to the construct with the nos terminator, no quantitative GUS assay was performed.

To rule out background GUS staining in the plants due to potential bacterial activity, Agrobacterium carrying the pBMG305, pBMM347, pBMGU1, pBMGIU44, pBMMU12, pBMMInU11, pBMMIU32, pBMU2, pBI101 and pBI121 constructs were assayed for GUS activity. As expected none of the tested Agrobacteria carrying the Msg-intron constructs express intron constructs express GUS. The constructs with promoters but without intron did express GUS. Surprisingly, the bacteria carrying the pBI101 and pBMU2 plasmids, both without a promoter directly 5' of uidA, expressed GUS. Without wishing to be bound by theory, it is believed that this is due to a read through from the nos promoter that drives nptII, because it is in the same direction as and upstream of uidA. There is a nos-terminator, but the bacterium might ignore this. The pBI101 construct has never resulted in GUS expression in Arabidopsis.

Msg shows a high level of expression in soybean pod tissue. The Msg gene has significant homology with the major latex protein (MLP) homologs, a family of flower and fruit specific genes for which the function of the gene products are unknown. The first major latex protein reported was from opium poppy, *Papaver somniferum*, where it is present at high levels in the latex [Griffing and Nessler (1989) *J. Plant Physiol.* 134:357–363; Nessler et al. (1990) supra; Nessler et al. (1990) *Plant Mol. Biol.* 15:951–953; Nessler and Burnett (1992) *Plant Mol. Biol.* 20:749–752; Nessler, C. L. (1994) *Gene* 139:207–209] a substance believed to have a protective function to the plant. Homologs are also reported in tobacco [Meeks-Wagner et al. (1989) supra; Neale et al. (1990) supra], bell pepper, *Capsicum annuum* [Pozueta-Romero et al. (1995) supra], melon *Cucumis melo* [Aggelis et al. (1997) supra], and wild strawberry, *Fragaria vesca* [Nam et al. (1999) supra]. Curiously, latex is not a feature of every plant in which these genes have been found.

These homologs are similar in size and location of the intron and no obvious signal peptides have been found in any of them. In the opium poppy however, the proteins have been localized to membrane bound vesicles in the laticifers [Griffing and Nessler (1989) supra] and the Sn-1 of bell pepper has been shown to be associated with small vacuoles close to the plasmalemma [Pozueta-Romero (1995) supra]. The tobacco FB7–4 was initially reported to be expressed during floral initiation [Meeks-Wagner (1989) supra] and was later shown to be highly expressed in the basal internodes of the stem [Neale et al. (1990) supra]. The melon MEL7 gene and the strawberry 3.1. R4 gene are highly expressed in ripening fruits but also to some extent in root and stem [Aggelis et al. (1997) supra; Nam et al. (1999) supra, respectively]. In poppy, the major latex proteins are reported to be highly expressed in flower buds and weakly in roots and in the laticifers [Nessler and Burnett (1992) supra], which are present throughout the poppy plant.

The major latex protein homologs also show significant homology to major pollen allergen proteins and other pathogenesis-related (PR) proteins (Cor a I of hazel [Breiteneder et al. (1993) supra]; Car bI of hornbeam [Larsen et al. (1992) supra]; ribonuclease of ginseng, [Moiseyev et al. (1997) supra]; Api g I of celery, [Breiteneder et al. (1995) supra]; parsley PR1, [Rushton et al. (1996) supra]. Especially the intracellular pathogenesis related proteins, the IPR-P's, seem to have an interesting relation to the major latex protein homologs as recently reviewed by [Osmark et al. (1998) supra]. The homology between the two gene families is not more than about 25% but they have similar structures, sizes and pI's and their functions are unknown [Osmark et al. (1998) supra]. There is an IPR protein reported for soybean, the SAM22 [Crowell et al. (1992) *Plant Mol. Biol.* 18:459–466], which makes our report the first report of a plant that has representative genes from both the MLP family and the IPR family. SAM22 is highly expressed in roots but is also expressed in leaves after wounding [Crowell et al. (1992) supra]. The soybean SAM22 and Msg proteins show a 25.3% sequence identity.

We have shown in transient expression assays that the promoter from the Msg-gene can function as a strong activator of GUS in soybean and green bean pods following particle bombardment (FIG. 7). Control bombardment of leaves and cotyledons did not result in GUS expression. The transient experiments agree well with the expression of Msg transcripts as determined by RNA blots (FIG. 1), in which there is strong expression in the pods but not in the expanded leaves or in the developing cotyledons. Some expression is detected in nodes, but it is not clear if this is due to Msg or the second related gene that is detected by DNA blotting.

In contrast to the transient soybean transformation, maximal tissue-specific expression in stable Arabidopsis transformants required about 2.26 kb of the Msg-promoter. The expression was localized to nodes between pedicel and stem, or cauline leaf and stem, to nectaries, short style and to guard cells of the stem, pedicel and silique. GUS expression was never seen in rosette leaves or roots. Guard cell specific expression is reported for genes involved in different tasks. Guard cells of transgenic tobacco are reported to express GUS driven by a 2753 bp fragment of the tomato tas14 promoter [del Mar Parra et al. (1996) *Plant Mol. Biol.* 32:453–460]. The tas14 gene is an inducible dehydrin involved in water stress, but it is also developmentally expressed in flowers and pollen. The promoter of an Arabidopsis acidic chitinase also activates GUS in guard cells of transgenic Arabidopsis [Samac and Shah (1991) *Plant Cell* 3:1063–1072]. Stomates are natural openings through which pathogens can intrude, and chitinase is involved in the plants primary defense against pathogens. Expression due to the chitinase promoter is also seen in anthers [Samac and Shah (1991) supra]. Expression of GUS in guard cells of different floral organs and the receptacle is observed when the GUS gene is driven by the promoter region of the rha1 gene from Arabidopsis [Terryn et al. (1993) *Plant Cell* 5:1761–1769]. The rha1 gene encodes a small GTP binding protein involved in secretion and vesicle-mediated transport.

The relationship of the major latex homologs to the PR proteins and allergens and the activity of the Msg promoter in guard cells, fruit and floral organs reflects the defense and/or stress function of the Msg gene product.

Tissue-specific expression in plants is assumed to be the result of combinatorial regulation due to the specific set of regions present in the promoter [Singh, K. B. (1998) supra]. Many previously reported promoters are shown to have distal quantitative regions and proximal tissue-specific regions [Stougaard et al. (1987) supra; Bustos et al. (1989) *Plant Cell* 1:839–853, Zhao et al. (1994) supra; Hamilton et al. (1998) supra; Ruiz-Rivero and Prat (1998) supra]. However, this may not be a strict rule. In the case of two fruit ripening-specific genes (E4 and E8) from tomato, sites flanking the genes were shown to contain protein binding sites. The genes are simultaneously expressed but the positions of the binding sites in the 5'-regions of the two genes differed by 900 bp [Cordes et al. (1989) *Plant Cell* 1:1025–1034; Deikman et al. (1998) *Plant Mol. Biol.* 37:1001–1011]. Our results also show that the tissue-specificity does not necessarily have to be confined to the most proximal region of a promoter but can be located farther upstream. The Msg-promoter gains expression in specific tissues with the addition of increasing amounts of 5'-sequence (FIGS. 7 and 8).

Figure 8:
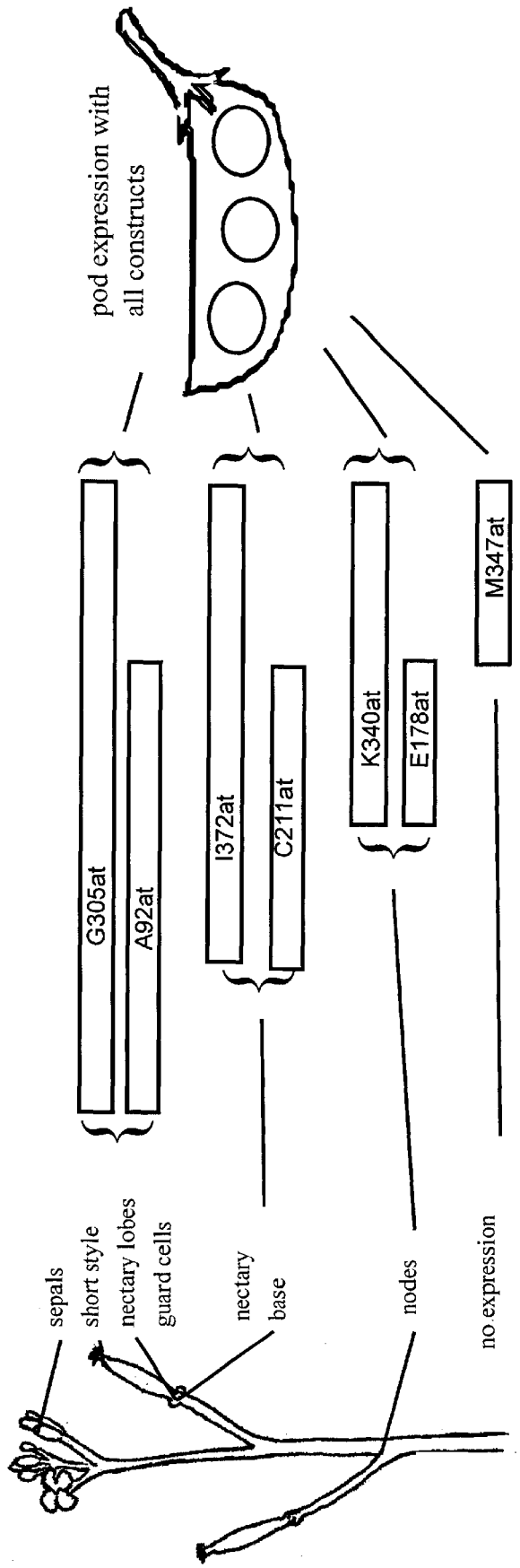
FIG. 8 shows that 5'-deletions of the Msg-promoter lead to loss of expression in various Arabidopsis cell types. Tissue-specific expression in Arabidopsis plants transformed with the indicated deletions. All constructs tested for transient expression in soybean activate GUS in pods but not in leaves.
Figure 9A:
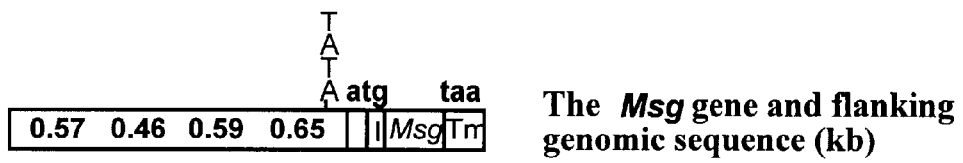
FIGS. 9A–9E summarize the Msg gene and DNA constructs with deletion analysis of the 5'UTR, 3'UTR constructs and intron constructs.
Figure 9B:
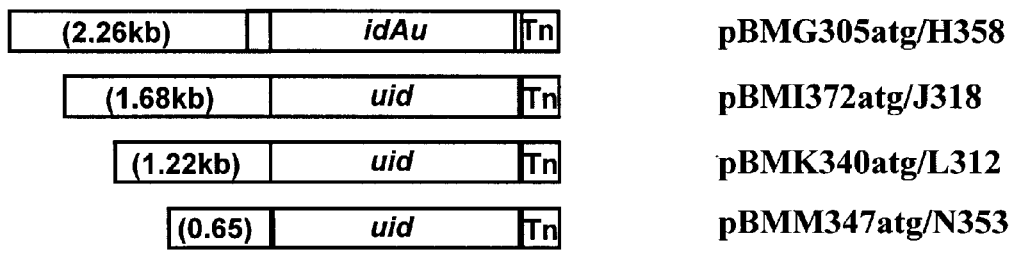
Figure 9C:
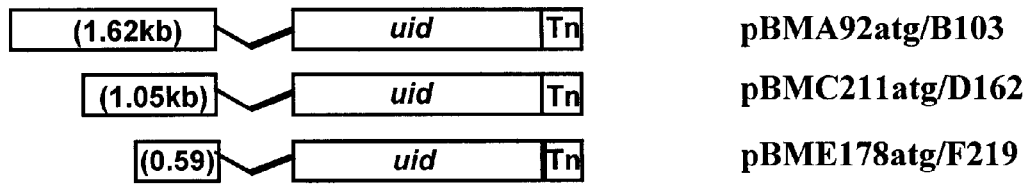
Figure 9D:
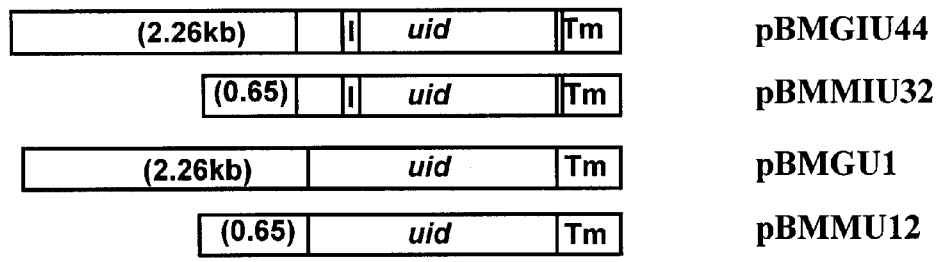
Figure 9E:
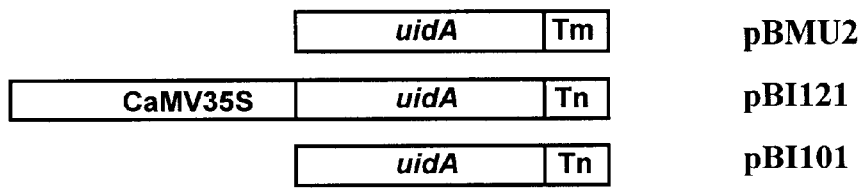

Surprisingly, our stable transformation experiments show that the proximal 650 bp alone does not induce gene expression at all in Arabidopsis as illustrated in FIG. 8, although it can transiently direct expression of GUS in soybean pods by particle bombardment. In fact, including this region in the promoter does not alter the pattern of organ/tissue-specificity either. The transformants of the constructs including the 650 bp show the same pattern as do the transformants of the counterpart constructs without the 650 bp. From both the transient expression experiment in soybean and the stable transformation of Arabidopsis, we conclude that including the 650 bp enhances the expression of the GUS reporter gene. These results indicate (1) that the A/T-rich proximal 650 bp region contains transcription enhancer elements; (2) that the 590 bp region just upstream of the proximal 650 bp contains regions that can take over the basic promotion functions (i.e. TATA box etc.); and (3) that the conserved repeats found in the most distal 570 bp (2 kb upstream of the start codon) are responsible for the specificity of expression in the style, nectaries and guard cells in Arabidopsis. The 650 bp region coupled with the Msg 3'UTR directed expression in the filaments of stamens.

Small repeated motifs have been reported from other regulating domains in tissue-specific promoters such as the β-phaseolin storage protein of bean [Bustos et al. (1991) *EMBO J.* 10: 1469–1479]. For the same β-phaseolin promoter, A/T-rich domains have been reported to enhance transcription [Bustos et al. (1989) *Plant Cell* 1:839–853]. A/T-rich regions of the tissue-specific pea plastocyanin (PetE) gene promoter have recently been shown to enhance transcription, whether fused upstream or downstream of a cauliflower mosaic virus 35S minimal promoter [Sandhu et al. (1998) *Plant Mol. Biol.* 37:885–896]. There are also reports of A/T-rich enhancing promoter regions in soybean heat shock proteins [Czarnecka et al. (1992) *Plant Mol. Biol.* 19:985–1000]. Interestingly, regions about −500 bp upstream of the transcription start in a soybean heat shock promoter [Schöffl et al. (1984) supra] show 70% homology to a region −700 to −800 bp upstream of the translational start of the Msg-promoter.

Regions upstream of the proximal 650 bp can take over the function of the true TATA box, as we have shown with the 650 bp proximal deletion constructs. These upstream regions are relatively AT-rich and there is a possibility that alternative TATA-box-like elements reside there. However, there is also the possibility that there may be other protein binding elements that can help initiate transcription as in TATA-less promoters. Such systems have been reported from other organisms [Wieczorek et al. (1 998) supra].

The Msg-promoter behaves differently in stably transformed Arabidopsis and transiently in soybean. This indicates the importance of well-defined regulating sequences useful for species other than model plants. Tissue-specific regulation in different plants might occur in different tissues due to differences in sets of organs and in function of the organ. Soybean does not have nectaries, and the function of the gene product is apparently carried out in the pod though the cell type in the pod has yet to be determined. However, based on the expression pattern and the high level of expression, the Msg-promoter is a useful promoter to drive transgene expression in pods of not only soybean but also other legumes and other plants having similar fruit anatomy.

In summary, we have identified a soybean equivalent of the major latex protein homologs and hereby reported the first plant to have both a major latex protein (MLP) homologue in addition to an intracellular pathogenesis-related protein (IPR-P). The Msg gene product is unknown, but it is highly expressed in soybean pods. We have shown that the promoter contains different regions important for maximal expression of GUS in a heterologous plant, but that surprisingly, the 650 bp adjacent to the translation start codon does not affect the pattern of expression.

Transgenic T3 generation Arabidopsis plants transformed with the 650 bp minimal Msg promoter, uidA and nos terminator (pBMM347atg), or with the 2.26 kb full length Msg promoter, uidA and nos terminator (pBMG305atg) were used to see if there are pathogen-inducible elements in the Msg promoter. Table 3A–3B show the results of the experiment. In the infiltrated plants, no difference in GUS signal was seen with any of the constructs as compared to the blank control (no bacteria) sample which showed typical expression. The pBMM347atg-plants showed no GUS activity at all, and the pBMG305atg-plants showed the typical guard cell and nectary expression. Sometimes there was also some weak expression observed in the epidermis of the mid vein in the leaves on the pBMG305atg-plants infiltrated with avr+. The controls, T2 generation of Arabidopsis transformed with the promoterless:uidA pBI101 or 35S:uidA pBI121, showed the expected no expression and constitutive expression respectively. There was no significant difference in appearance between the plants infiltrated with *P. fluorescens, P. syringae* avr+ or avr−, but the blank control plants looked somewhat healthier.

The hypersensitive response experiment (Table 3B) shows the same result as the infiltration experiment. There was no difference observed between the GUS expression in the inoculated plants and the blank control plants inoculated with buffer only. No difference was seen between the plants inoculated with the different bacterial strains either. Furthermore, the half of the leaves that were hand-inoculated appeared unhealthy or dying, but the plants did not appear to show any induction of GUS due to wounding of the leaves.

Pieces of soybean pod, stem and nodes were fixed and dehydrated, subjected to prehybridization treatments, and then they were subjected to in situ hybridization of the Msg transcript. The lambda cDNA clone VS-107 was used as a template to generate the sense and anti-sense probes. The sample is the tissue hybridized with the anti-sense SP6 transcript of VS-107. The controls used were as follows 1) tissue hybridized with VS-107 (T7) sense probe; 2) tissue sample treated like the others but with no probe and no antibody to localize endogenous phosphatase activity; 3) tissue sample with no probe but with antibody to localize signal due to unspecific binding of the anti-body to the tissue; 4) tissue hybridized with sense vector probe; 5) tissue hybridized with anti-sense vector probe; 6) tissue hybridized with clone b22 (low copy soybean gene) sense probe; 7) tissue hybridized with b22 anti-sense probe. A continuous layer of cells which is likely to be the mid pericarp layer is present in the mesocarp. Unspecific binding of the anti-body can be seen as a dark band in the endocarp. The endocarp band can also be seen in the control sample that was treated with anti-body but no probe. No controls except the T7 Msg transcript had a signal in the mid pericarp layer. No guard cells on pods, stem or node showed a signal.

To show that the signal in the pod was not in the vascular tissue, staining for lignin with phloroglucinol was performed. The vascular bundles can be seen as red streaks in the pod wall inside (seed side) of the continuous mid pericarp layer. Another indicative feature is that the vascular bundles are not in a continuous layer throughout the cross sections of the pod as is the mid pericarp layer.

*Pseudomonas syringae* has been reported to induce expression of pathogenesis related genes in Arabidopsis (See, e.g., Yu et al. (1998) Proc. Nati. Acad. Sci. USA 95, 7819–7824). Accordingly, *P. syringae* was tested to determine whether it can induce reporter gene expression where the Msg-promoter is fused to uidA in transgenic Arabidopsis. Arabidopsis plants transformed with the full length promoter construct pBMG305atg or 650 bp minimal promoter construct pBMM347atg were chosen to represent the Msg-promoter. Arabidopsis transformed with pBI101 (promoterless GUS) and pBI121 (35S GUS) were used as negative controls. Blank controls were also included with transformants of all constructs inoculated with buffer only. There was no difference in expression between the blank control infiltrations and inoculations and the plants infiltrated with the avr+ and avr– *P. syringae* strains. Neither were there any differences whether the plants were infiltrated with a regular *P. syringae* strain (DC3000) or hand-inoculated with a *P. syringae* strain (race 4) that causes a hyper sensitive response in Arabidopsis. Inoculation with the non pathogenic *P. fluorescens* (strain 1855-344, Hwang and Farrand 1994, vide infra) that was used as a control lead to the same non induced appearance as the *P. syringae* inoculated plants. Since no differences could be observed, no evidence of the Msg-promoter being pathogen- or wound-induced resulted from this experiment. There is a possibility that there are differences between the pathogen response mechanism in Arabidopsis and in soybean and this is why there was no induction in Arabidopsis. Another possibility is that the promoter is induced by other pathogens than bacteria, such as fungi or viruses and Pseudomonas is not the right pathogen. The third possibility is that although the 5'upstream region is enough to give tissue specificity, it is not enough for pathogen induction and other regulatory regions such as the intron or the 3'UTR are needed. It is very likely that there are pathogenesis related genes that are constantly turned on in a preventative purpose and that Msg belongs to this group. It has been suggested that it is indeed very common that pathogenesis related genes apart from accumulating in response to pathogens in leaves, also have a developmental function in flowers and abscission zones as a barrier for "safety zones" to restrict pathogens spreading [Eyal et al. (1993) Plant J. 4, 225–234]. Whether the Msg-promoter is inducible or not, the relatively high expression in the tissues prone to infection still makes it a good candidate for driving anti-disease genes.

The Msg transcript has been localized to a single cell layer in the pod and to the inner epidermis. The single cell layer in the pod has been identified as the mid pericarp layer. This layer was recently described in soybean pods as a single cell layer in the middle of the mesocarp [Dubbs and Grimes (2000) Plant Physiol., 123, 1269–1280; ibid. 123, 1281–1288]. It was detected because three isoforms of soybean lipoxygenase (VLXA, B and C, VLX =vegetative lipoxygenase) were localized specifically to the cytosol there. Lipoxygenases are a group of proteins that have different functions such as plant defense, nitrogen partitioning and storage and enzyme activity for oxidizing lipids. There are at least eight different isoforms in soybean and they appear to have different functions as they are expressed in different tissues [Fischer et al. (1999) Plant J. 19 543–554; Dubbs and Grimes (2000) supra]. One isoform, VLXD seems to have a function as a vegetative storage protein in leaves [Fischer et al. (1999) supra] where it has been shown to be expressed in the paraveinal mesophyll [Stephenson et al. (1998) Plant Physiol. 116, 923–933]. The mid pericap layer could be analogous to the leaf paraveinal mesophyll layer which is a single cell layer as well. Expression of Msg in leaves has never been seen, but it can not be excluded that there is not a homologue of Msg in the leaf having so low similarity that it does not hybridize on a DNA blot. If the high expression observed in total pod RNA is confined to the mid pericarp layer, the expression of Msg in this layer must be extremely high. The lipoxygenases are reported to consist of about 40% of the total protein in the pod exudate [Dubbs and Grimes (2000) supra].

The mid pericarp layer is likely to have a fruit protecting or pathogen defense function [Dubbs and Grimes (2000) supra] much like laticifers do. Laticifers, latex containing cells or cell layers, are distributed among a number of plant families. Two of the more famous plants with latex of interest for humans are opium poppy (*Papaver somniferum*) and the rubber tree (*Hevea brasiliensis*). Latex from different plants can have a composition of a wide variety of substances such as enzymes and secondary metabolites. The different latex components have different functions, some may be directly anti-pathogenic while others may have a function to clog wounded areas to stop invasion or drying out. Soybean has not been reported to have latex and laticifers, but the mid pericarp layer may be an analogous tissue.

Another organ that has not typically been connected with soybean are nectaries, although extrafloral nectaries are reported to be abundant in Leguminosae (i.e. Fabaceae). Pascal et al. (2000) A. J. Bot. 87, 327–338 reports that Desmodium, a relative of soybean, has stalked elevated nectaries on their rachis. Floral nectaries have commonly been ascribed a pollinator attracting function. Insects such as flies, bees and butterflies and even higher animals such as bats and birds are common pollinators and the nectar composition can be "custom designed" for the type of pollinator associated with a particular plant species. Nectaries can be floral or extrafloral depending on the function. Obviously, extrafloral nectaries must have different functions than attracting pollinators. Floral nectaries can be an entry point for fungal pathogens such as reported for *Aspergillus flavus* in cotton [Klich (1990) Appl. Environ. Microbiol. 56, 2499–2502]. The function of extrafloral nectaries may be to secrete anti-fungal or anti-bacterial substances at sites prone to infection such as the cotyledonary nodes [Klich (1990) supra]. The activity of the Msg-promoter in Arabidopsis nodes and floral nectaries is consistent with a defense function of the Msg-gene, localized to the mid pericarp layer in soybean pods.

In the in situ hybridization experiments, no expression was seen in soybean guard cells but this may reflect potentially different entries of pathogens or defense against different pathogens in the two plants. There is also the possibility that there are technical difficulties with in situ localization in guard cells. Thoma et al. (1994) Plant Physiol. 105, 35–45 reports that in Arabidopsis, GUS expression resulted from the Arabidopsis lipid transfer protein LTP1-promoter in, among other tissues, guard cells, stipules and nectaries, and that subsequently, expression of the GUS protein could not be detected in these tissues by in situ hybridizations.

It is surprising that Arabidopsis and some other members of Brassicaceae have functional nectaries with plenty of hexoses because they are mostly self pollinated, and there is speculation that nectaries evolved earlier than self pollination in Arabidopsis [Davies et al. (1998) Planta 205, 305–318].

A soybean root homologue of Msg reported in GenBank (clone G08, Accession No. AAD50376) was isolated as a transcriptionally regulated gene during soybean and soybean cyst nematode interactions. The relatedness of this gene to the major latex proteins and the intracellular pathogenesis related proteins may provide another clue to a possible pathogen defense function.

Based on the localization to the midpericarp layer and in Arabidopsis nectaries, nodes, nectaries, guard cells and sometimes hydatodes, the relatedness to the intracellular pathogenesis related proteins and allergens and the relatedness to the soybean cyst nematode related gene G08, the conclusion is that the Msg is probably involved in pathogen defense and that it is localized to the mid pericarp layer which is a putative analog of articulated laticifers. This is likely to be a compartment or barrier of great importance with the function to protect the developing seeds from pathogens.

It is also understood by the skilled artisan that there can be limited numbers of nucleotide substitutions in a transcription regulating sequence without significantly affecting function, and that Msg transcription regulatory sequences can have some nucleotide sequence divergence from the specifically exemplified sequence. Naturally occurring variants can be identified, e.g., by hybridization to the exemplified Msg transcription regulatory sequence (or a portion thereof capable of specific hybridization to Msg transcription regulatory. sequences) under conditions appropriate to detect at least about 70% nucleotide sequence homology, preferably about 80%, more preferably about 90% or 95–100% sequence homology. The tissue specific regulation can be confirmed by using the methods described hereinbelow. Preferably the transcription regulatory sequence has at least about 90% nucleotide sequence identity to the exemplified sequence.

It is well known in the biological arts that certain amino acid substitutions can be made in protein sequences without affecting the function of the protein. Generally, conservative amino acids are tolerated without affecting protein function. Similar amino acids can be those that are similar in size and/or charge properties, for example, aspartate and glutamate and isoleucine and valine are both pairs of similar amino acids. Similarity between amino acid pairs has been assessed in the art in a number of ways. For example, Dayhoff et al. (1978) in *Atlas of protein Sequence and Structure*, Volume 5, Supplement 3, Chapter 22, pp. 345–352, which is incorporated by reference herein, provides frequency tables for amino acid substitutions which can be employed as a measure of amino acid similarity. Dayhoff et al.'s frequency tables are based on comparisons of amino acid sequences for proteins having the same function from a variety of evolutionarily different sources.

A polynucleotide or fragment thereof is substantially homologous (or substantially similar) to another polynucleotide if, when optimally aligned (with appropriate nucleotide insertions or deletions) with another polynucleotide, there is nucleotide sequence identity for approximately 85% of the nucleotide bases, preferably about 90%, and more preferably about 95% to 100% of the nucleotide bases of the specifically exemplified 5" or 3" transcription regulatory sequences.

DNA molecules with at least 85% nucleotide sequence identity to a specifically exemplified Msg transcription regulatory sequence of the present invention can be identified by hybridization under stringent conditions using a probe having one of the specifically exemplified transcription regulatory sequences of the present invention. Stringent conditions involve hybridization at a temperature between 65 and 68C in aqueous solution (5×SSC, 5×Denhardt's solution, 1% sodium dodecyl sulfate) or at about 42C in 50% formamide solution, with washes in 0.2×SSC, 0.1% sodium dodecyl sulfate at room temperature, for example. The ability of a sequence related to the specifically exemplified transcription regulatory sequences of the present invention are readily tested by one of ordinary skill in the art using methods described in the Examples herein below to confirm that there is tissue-specific expression in at least one cell or tissue type of a plant, where the cell or tissue is one which is potential site of attack by a plant pathogen or other plant pest, especially cells of the developing seedpod, as well as guard cells, nectaries and node cells.

As used in the present context, percent homology or percent sequence identity of two nucleic acid molecules is determined using the algorithm of Karlin and Altschul (1990) Proc. Natl. Acad. Sci. USA 87, 2264–2268, modified as described in Karlin and Altschul (1993) Proc. Natl. Acad. Sci. USA 90, 5873–5877. Such an algorithm is incorporated into the NBLAST and XBLAST programs of Altschul et al. (1990) J. Mol. Biol. 215, 402–410. BLAST nucleotide searches are performed with the NBLAST program, scor=100, wordlength=12, to obtain nucleotide sequences homologous to the nucleotide sequences of the present invention. BLAST protein searches are performed with the XBLAST program, score=50, wordlength=3, to obtain amino acid sequences homologous to a reference polypeptide sequence. To obtain gapped alignments for comparison purposes, Gapped BLAST is utilized as described in Altschul et al. (1997) Nucl. Acids Res. 25, 3389–3402/When using BLAST and Gapped BLAST programs, the default parameters of the respective programs (XBLAST and NBLAST) are used. Gaps introduced to optimize alignments are treated as mismatches in calculating identity. See, e.g., the website of the National Center for Biotechnology Information.

An isolated or substantially pure polynucleotide is a polynucleotide which is substantially separated from other polynucleotide sequences which naturally accompany a native Msg protein coding sequence). The term embraces a polynucleotide sequence which has been removed from its naturally occurring environment, and includes recombinant or cloned DNA isolates, chemically synthesized analogues and analogues biologically synthesized by heterologous systems.

A polynucleotide is said to encode a polypeptide if, in its native state or when manipulated by methods known to those skilled in the art, it can be transcribed and/or translated to produce the polypeptide of a fragment thereof. The antisense strand of such a polynucleotide is also said to encode the sequence.

A nucleotide sequence is operably linked when it is placed into a functional relationship with another nucleotide sequence. For instance, a promoter is operably linked to a coding sequence if the promoter affects its transcription or expression. Generally, operably linked means that the sequences being linked are contiguous and, where necessary to join two protein coding regions, contiguous and in reading frame. However, it is well known that certain genetic elements, such as enhancers, may be operably linked even at a distance, i.e., even if not contiguous.

The term non-naturally occurring or recombinant nucleic acid molecule refers to a polynucleotide which is made by the combination of two otherwise separated segments of sequence accomplished by the artificial manipulation of isolated segments of polynucleotides by genetic engineering techniques or by chemical synthesis. In so doing one joins together polynucleotide segments of desired functions to generate a desired combination of functions.

Polynucleotide probes include an isolated polynucleotide attached to a label or reporter molecule and may be used to identify and isolate other legume Msg protein coding sequences. Probes comprising synthetic oligonucleotides or other polynucleotides may be derived from naturally occurring or recombinant single or double stranded nucleic acids or be chemically synthesized, and they may be used in polymerase chain reactions as well as in hybridizations. Polynucleotide probes may be labeled by any of the methods known in the art, e.g., random hexamer labeling, nick translation, or the Klenow fill-in reaction. Oligonucleotides or polynucleotide primers useful in PCR are readily understood and accessible to the skilled artisan using the sequence information provided herein taken with what is well known to the art.

Large amounts of the polynucleotides may be produced by replication in a suitable host cell. Natural or synthetic DNA fragments coding for a Msg protein or other protein of interest incorporated into recombinant polynucleotide constructs, typically DNA constructs, capable of introduction into and replication in a prokaryotic or eukaryotic cell, desirably a yeast cell, and preferably a plant cell. Usually the construct will be suitable for replication in a unicellular host, such as yeast or bacteria, but a multicellular eukaryotic host may also be appropriate, with or without integration within the genome of the host cells. Commonly used prokaryotic hosts include strains of *Escherichia coli*, although other prokaryotes, such as *Bacillus subtilis* or Pseudomonas, may also be used. Mammalian or other eukaryotic host cells include filamentous fungi, plant, insect, amphibian and avian species. Such factors as ease of manipulation, ability to appropriately glycosylate expressed proteins, degree and control of protein expression, ease of purification of expressed proteins away from cellular contaminants or other factors may determine the choice of the host cell.

The polynucleotides may also be produced by chemical synthesis, e.g., by the phosphoramidite method described by Beaucage and Caruthers (1981) *Tetra. Letts.* 22:1859–1862 or the triester method according to Matteuci et al. (1981) *J. Am. Chem. Soc.* 103:3185, and may be performed on commercial automated oligonucleotide synthesizers. A double-stranded fragment may be obtained from the single 'stranded product of chemical synthesis either by synthesizing the complementary strand and annealing the strand together under appropriate conditions or by adding the complementary strand using DNA polymerase with an appropriate primer sequence.

DNA constructs prepared for introduction into a prokaryotic or eukaryotic host cell typically comprise a replication system (i.e. vector) recognized by the host, including the intended DNA fragment encoding the desired polypeptide, and preferably also include transcription and translational initiation regulatory sequences operably linked to the Msg or other protein-encoding segment. Expression systems (expression vectors) may include, for example, an origin of replication or autonomously replicating sequence (ARS) and expression control sequences, a promoter, an enhancer and necessary processing information sites, such as ribosome-binding sites, RNA splice sites, polyadenylation sites, transcriptional terminator sequences, and mRNA stabilizing sequences. Signal peptides may also be included where appropriate from secreted polypeptides of the same or related species, which allow the protein to cross and/or lodge in cell membranes or be secreted from the cell.

An appropriate promoter and other necessary vector sequences will be selected so as to be functional in the host. Examples of workable combinations of cell lines and expression vectors are described in Sambrook et al. (1989) vide infra; Ausubel et al. (Eds.) (1993) *Current Protocols in Molecular Biology*, Greene Publishing and Wiley Interscience, New York; and Metzger et al. (1988) *Nature* 334:31–36. Many useful vectors for expression in bacteria, yeast, mammalian, insect, plant or other cells are well known in the art and may be obtained such vendors as Stratagene, New England Biolabs, Promega, and others. In addition, the construct may be joined to an amplifiable gene (e.g., DHFR) so that multiple copies of the gene may be made. For appropriate enhancer and other expression control sequences, see also *Enhancers and Eukaryotic Gene Expression*, Cold Spring Harbor Press, NY (1983). While such expression vectors may replicate autonomously, they may less preferably replicate by being inserted into the genome of the host cell.

Expression and cloning vectors desirably contains a selectable marker, that is, a gene encoding a protein necessary for the survival or growth of a host cell transformed with the vector. Although such a marker gene may be carried on another polynucleotide sequence co-introduced into the host cell, it is most often contained on the cloning vector. Only those host cells into which the marker gene has been introduced will survive and/or grow under selective conditions. Typical selection genes encode proteins that (a) confer resistance to antibiotics or other toxic substances, e.g., ampicillin, gentamycin, bleomycin, hygromycin, neomycin, methotrexate, etc.; (b) complement auxotrophic deficiencies; or (c) supply critical nutrients not available from complex media. The choice of the proper selectable marker will depend on the host cell; appropriate markers for different hosts are known in the art.

The DNA constructs containing a nucleotide sequence to be expressed under the control of the Msg transcription regulatory sequences of the present invention can be introduced (transformed, transfected) into the host cell by any of a number of appropriate means, including electroporation; transformation or transfection employing calcium chloride, rubidium chloride, calcium phosphate, DEAE-dextran, or other substances; microprojectile bombardment; lipofection; and transfection or infection (where the vector is an infectious agent, such as a viral genome). The choice of such means depends on the choice of host cell. Large quantities of the polynucleotides and polypeptides of the present invention may be prepared by transforming suitable prokaryotic or eukaryotic host cells with legume Msg protein-encoding polynucleotides of the present invention in compatible vectors or other expression vehicles and culturing such transformed host cells under conditions suitable to attain expression of the desired sequence.

In order to eliminate 5' untranslated and signal sequences at the 5' side of the coding sequence, a combination of restriction endonuclease cutting and site-directed mutagenesis via PCR using an oligonucleotide containing a desired restriction site for cloning (one not present in coding sequence), a ribosome binding site, an translation initiation codon (ATG) and the codons for the first amino acids of a Msg protein or other protein of interest. The oligonucleotide for site-directed mutagenesis at the 3' end of the coding sequence for the Msg protein includes nucleotides encoding the carboxyterminal amino acids of the coding sequence of interest, a translation termination codon (TAA, TGA or TAG), and a second suitable restriction endonuclease recognition site not present in the remainder of the DNA sequence to be inserted into the expression vector. A site-directed mutagenesis strategy is described, for example, in Boone et al. (1990) *Proc. Natl. Acad Sci. USA* 87:2800–2804, with modifications for use with PCR as readily understood by the skilled artisan.

The skilled artisan understands that it may be advantageous to modify the exemplified Msg transcription regulatory sequence or Msg protein coding sequence for improved expression in a particular recombinant host cell. Such modifications, which can be carried out without the expense of undue experimentation using the present disclosure taken with knowledge and techniques readily accessible in the art, can include adapting codon usage so that the modified coding sequence has codon usage substantially like that known for the target host cell. Such modifications can be effected by chemical synthesis of a coding sequence synonymous with the exemplified coding sequence or by oligonucleotide site-directed mutagenesis of selected portions of the coding sequence.

A transgenic plant is one which has been genetically modified to contain and express heterologous DNA sequences, either as regulatory RNA molecules or as proteins. As specifically exemplified herein, a transgenic plant is genetically modified to contain and express a heterologous DNA sequence operably linked to and under the regulatory control of transcriptional control sequences by which it is not normally regulated, i.e., under the regulatory control of the tissue-specific transcriptional control sequences of the Msg gene, for example, of *Glycine max*. The genes corresponding to the soybean Msg gene can be isolated from other legumes, and can be used in place of the specifically exemplified Msg coding sequence or transcription regulatory sequences of the present invention. The present invention provides for the expression of a nucleotide sequence of interest expressed under the regulatory control of transcription regulatory sequences expressed in the developing seedpod, preferably of a legume or developing fruit of a plant. As specifically exemplified, the regulatory sequences are those of the Msg gene of *Glycine max*. As used herein, a transgenic plant also refers to those progeny of the initial transgenic plant which carry and are capable of expressing the heterologous coding sequence under the regulatory control of the qualitative and/or quantitative Msg transcription control sequences described herein. Seeds containing transgenic embryos are encompassed within this definition. Transgenic seeds and transgenic embryos are those which contain a specifically regulated DNA construct of the present invention. In the context of the present application, it is understood that the expression cassette is stably maintained in the genome of a transformed host plant cell, plant tissue and/or plant.

The term transgenic plant, as used herein, refers to a plant which has been genetically modified to contain and express heterologous DNA. As specifically exemplified herein, a transgenic plant is genetically modified to stably contain and consistently express in the developing seedpod the nucleotide sequence of interest that is not normally present in the plant. As further used herein, a transgenic plant also refers to progeny of the initial transgenic plant, which progeny carry and are capable of expressing the phenotype carried by an Msg-regulated expression product. As used herein, a transgenic plant is a monocotyledonous or a dicotyledonous plant. Transgenic plants of the present invention can include, without limitation, legumes or tobacco, cucumber, muskmelon, members of the Solanaceae, Linaceae, Papaveraceae, Brassicaceae, and certain Ranuculaceae, among others. Transgenic plant cells and transgenic plant tissue are similarly genetically modified to stably contain heterologous DNA.

A pod or seedpod, as used herein, is the structure which surrounds an ovule(s) of a plant. The methods and expression cassettes of the present invention are suited for producing plants which are improved in seed quality, yield and/or pest resistance due to the expression of a suitable pest or pathogen resistance protein in the seedpod, but not in the seed.

The invention relates generally to genetic engineering and, more particularly, to a means and method for making plant seed pods which are improved in their disease resistance or in their resistance to insect pests or plant parasitic nematodes or other plant pathogens and/or are improved in their dessication resistance.

It is an object of the present invention to provide compositions and methods for the regulation of gene expression in a tissue-specific and developmental stage-specific manner by transgenic means. This is accomplished by the stable introduction into the plant genome of an expression cassette in which a gene encoding a protein of interest or other nucleotide sequence to be expressed is operably linked to legume Msg transcription control sequences, desirably a soybean Msg transcription regulatory sequence, which mediate expression of the linked gene in the proper plant part at the appropriate time during development.

Also provided by the present invention is an expression cassette can be expressed in plant tissue after the introduction of the cassette into plant tissue. A preferred coding sequence of interest is that for a pest or pathogen resistance protein such as chitinase, an insecticidal protein, a latex protein, a lectin which binds to a particular pathogen, single chain antibodies which bind specific to particular pathogen antigens, antimicrobial peptides such as Snakin-1 peptide from potato tubers [Segura et al. (1999) *Mol. Plant Microbe Interact* 12:16–23], the MIAMPI from Macadamia nut kernels [Marcus et al. (1997) *Eur. J. Biochem.* 244:743–749] and other antimicrobial peptides [For review, see Rao, A.G. (1995) *Mol. Biol. Plant Microb. Interact.* 8:6–13]. Transcription is regulated by an Msg transcriptional regulatory sequence from *Glycine max*), as specifically exemplified herein.

A further aspect of the present invention are transgenic plant cells, plant tissue and plants which have been genetically engineered to contain and express a nucleotide sequence of interest under the regulatory control of the tissue-specific Msg transcription regulatory element, such that the sequence of interest is selectively expressed in the developing seedpod such that the fruit (but not the seed) so produced contains the expressed sequence.

The present invention provides a method for the production of seedpods expressing a desired heterologous nucleotide sequence, said method comprising the steps of constructing an expression cassette in which a nucleotide sequence of interest is operably linked to an Msg transcriptional regulatory sequence, which transcription regulatory sequence mediates the expression of a downstream coding sequence in a developing seedpod, stably incorporating the expression cassette into a plant cell to produce a stably transformed plant cell and regenerating a transgenic plant from the stably transformed plant cell, whereby seedpods improved in their resistance to plant pests or pathogens are produced when the transgenic plant is cultivated.

The Msg transcriptional regulatory sequence mediates tissue-specific expression of an operably linked downstream coding sequence in developing legume seedpods, and in the seedpods of other plants. The Msg upstream untranslated region from about −2260 to about −1690 includes sequences which direct expression in sepals, short style nectary lobes and guard cells, in transgenic plants, e.g., Arabidopsis. The region between about −1690 and about −1100 includes sequences which direct expression in the nectary base, and the region between about −1100 and about −650 contains sequences which direct expression in nodes of transgenic Arabidopsis. The region between about −650 and −1 was not able to direct expression in seedpods or the aforementioned parts of Arabidopsis.

The present invention further provides a transgenic plant which has been genetically engineered to contain and express a nucleotide sequence of interest in the developing seedpod of a plant, e.g. legume, under the regulatory control of a tissue-specific Msg transcription regulatory sequence which is selectively expressing -in developing seedpod. Seeds and embryos containing the genetically engineered DNA construct (i.e., chimeric gene) of the present invention are within the intended definition of plant, as are progeny plants and seeds of progeny plants containing the DNA construct. Progeny plants include future generations of plants descended from an initial transgenic plant and containing the chimeric gene of the present invention. The nucleotide sequence heterologous to the Msg promoter can encode a protein which will improve resistance to a particular pathogen, or it can be a RNA molecule with a desired regulatory effect within the developing seedpod. Transgenic plants described herein comprise an Msg transcriptional regulatory sequence which mediates tissue-specific and developmental stage specific expression of an operably linked downstream -coding sequence. The transgenic plant producing seedpods improved in their resistance to plant pests can be a dicotyledonous plant or a monocotyledonous plant. Such a dicotyledonous plant can be a member of the Leguminaceae or the Solanaceae, including but not limited to *Lycopersicon esculentum*, or it can be any of a number of plants which produce seedpods similar in morphology and developmental pathway as the specifically exemplified soybean. Desirably the transgenic plant is a legume.

The Msg promoters used in the DNA constructs of the present invention may be modified, if desired, to affect their control characteristics. For purposes of this invention, the phrase promoter thus includes variations of the promoter, e.g., promoters derived by means of ligation with operator regions, random or controlled mutagenesis as well as tandem of multiple copies of enhancer elements, etc.

A coding sequence used in a DNA construct of this invention may be modified, if desired, to create mutants, either by random or controlled mutagenesis, using methods known to those skilled in the art. Those mutants can include synonymous coding sequences which have been modified to optimize the level of expression in a particular host cell, to create or remove restriction endonuclease recognition sites or to otherwise facilitate or accommodate molecular biological manipulations according to the knowledge of one of ordinary skill in the art. Such mutants and variants are therefore within the scope of the present invention.

The 3' non-translated region of a coding sequence of interest desirably contains a polyadenylation signal which functions to cause the addition of polyadenylate nucleotides to the 3' end of the RNA. Examples of suitable 3' regions are (1) the 3' transcribed, non-translated regions containing the polyadenylation signal of the tumor-inducing (Ti) plasmid genes of Agrobacterium, such as the nopaline synthase (NOS) gene, and (2) plant genes like the 7S soybean storage protein genes and the pea E9 small subunit of the RuBP carboxylase gene.

The mRNA produced by a DNA construct of the present invention also contains a 5' non-translated leader sequence. This sequence can be derived from the promoter selected to express the gene, and can be specifically modified so as to increase translation of the mRNA. The 5' non-translated regions can be obtained from viral RNAs, from suitable eukaryotic genes, or may be synthesized. The present invention is not limited to constructs, as presented in the following examples, wherein the non-translated region is derived from the 5' non-translated sequence that accompanies the promoter sequence. Rather, the non-translated leader sequence can be part of the 5' end of the non-translated region of the native coding sequence for the dsRNA-binding protein, or part of the promoter sequence, or can be derived from an unrelated promoter or coding sequence as discussed above.

While in most cases the heterologous DNA which is inserted into plant cells contains a gene which encodes a selectable marker such as an antibiotic resistance marker (e.g., the kanamycin/neomycin resistance determinant), this is not mandatory.

A DNA construct of the present invention can be inserted into the genome of a plant or animal by any suitable method. Such methods may involve, for example, the use of liposomes, electroporation, diffusion, particle bombardment, microinjection, gene gun, chemicals that increase free DNA uptake, e.g., calcium phosphate coprecipitation, viral vectors, and other techniques practiced in the art.

Suitable plant transformation vectors include those derived from a Ti plasmid of *Agrobacterium tumefaciens*, such as those disclosed by Bevan (1984) supra and EPO publication 120,516 [Schilperoort et al.]. In addition to plant transformation vectors derived from the Ti or root-inducing (Ri) plasmids of Agrobacterium, alternative methods can be used to insert the DNA constructs of this invention into plant cells.

A DNA construct prepared in accordance with the present invention is preferably introduced, via a suitable vector as described above, into cells or protoplasts derived from agriculturally important crops, e.g., dicotyledonous plants such as legumes, or other dicotyledonous or monocotyledonous plants.

The choice of vector in which the expression cassette of the present invention is operatively linked depends directly, as is well known in the art, on the functional properties desired, e.g., replication, protein expression, and the host cell to be transformed, these being limitations inherent in the art of constructing recombinant DNA molecules. In preferred embodiments, the vector utilized includes a prokaryotic replicon, i.e., a DNA sequence having the ability to direct autonomous replication and maintenance of the recombinant DNA molecule extra-chromosomally when introduced into a prokaryotic host cell, such as a bacterial host cell. Such replicons are well known in the art. In addition, preferred embodiments that include a prokaryotic replicon also include a gene whose expression confers a selective advantage, such as a drug resistance, to the bacterial host cell when introduced into those transformed cells. Typical bacterial drug resistance genes are those that confer resistance to ampicillin or tetracycline, among other selective agents. The neomycin phosphotransferase gene has the advantage that it is expressed in eukaryotic as well as prokaryotic cells.

Those vectors that include a prokaryotic replicon also typically include convenient restriction sites for insertion of a recombinant DNA molecule of the present invention. Typical of such bacterial vector plasmids are pUC8, pUC9, pBR322, and pBR329 available from BioRad Laboratories (Richmond, Calif.) and pPL, pK and K223 available from Pharmacia (Piscataway, N.J.), and pBLUESCRIPT and pBS available from Stratagene (La Jolla, Calif.). A vector of the present invention may also be a lambda phage vector including those lambda vectors described in *Molecular Cloning: A Laboratory Manual*, Second Edition, Maniatis et al., eds., Cold Spring Harbor, N.Y. (1989) and the lambda ZAP vectors commercially available, e.g., from Stratagene (La Jolla, Calif.). Other exemplary vectors include pCMU [Nilsson et al. (1989) *Cell* 58:707]. Other appropriate vectors may also be synthesized, according to known methods; for example, vectors pCMU/K$^b$ and pCMUII used in various applications herein are modifications of pCMUIV [Nilsson et al. (1989) supra].

Typical expression vectors capable of expressing a recombinant nucleic acid sequence in plant cells and capable of directing stable integration within the host plant cell include vectors derived from the tumor-inducing (Ti) plasmid of *Agrobacterium tumefaciens* described by Rogers et al. [(1987) *Meth. in Enzymol.* 153:253–277], and several other expression vector systems known to function in plants. See for example, Verma et al., Published PCT Application No. WO87/00551; Cocking and Davey Science (1987) 236:1259–1262.

In preferred embodiments, the plant cell expression vectors used include a selection marker that is effective in a eukaryotic cell, preferably a drug resistance selection marker. In preferred embodiments where a recombinant nucleic acid molecule of the present invention is expressed in plant cells, a preferred drug resistance marker is the gene whose expression results in kanamycin resistance, i.e., the chimeric gene containing nopaline synthetase promoter, Tn5 neomycin phosphotransferase II and nopaline synthetase 3' non-translated region described by Rogers et al. [(1988) In: *Methods for Plant Molecular Biology*, A. Weissbach and H. Weissbach, eds., Academic Press, Inc., San Diego, Calif.].

A transgenic plant can be produced by any means known to the art, including but not limited to *Agrobacterium tumefaciens*-mediated DNA transfer, preferably with a disarmed T-DNA vector, electroporation, direct DNA transfer, and particle bombardment [See Davey et al. (1989) *Plant Mol. Biol.* 13:275; Walden and Schell (1990) *Eur. J. Biochem.* 192:563; Joersbo and Burnstedt (1991) *Physiol. Plant.* 81:256; Potrykus (1991) *Annu. Rev. Plant Physiol. Plant Mol. Biol.* 42:205; Gasser and Fraley (1989) *Science* 244:1293; Leemans (1993) *Bio/Technology*. 11:522; Beck et al. (1993) *Bio/Technology*. 11: 1524; Koziel et al. (1993) *Bio/Technology*. 11:194; and Vasil et al. (1993) *Bio/Technology*. 11:1533.]. Techniques are well-known to the art for the introduction of DNA into monocots as well as dicots, as are the techniques for culturing such plant tissues and regenerating those tissues. Monocots which have been successfully transformed and regenerated include wheat, corn, rye, rice and asparagus. For example, U.S. Pat. No. 5,350,689 [Shillito et al. (1994)] describes transgenic *Zea mays* plants regenerated from protoplasts and protoplast-derived cells. For efficient production of transgenic plants, it is desired that the plant tissue used for transformation possess a high capacity for regeneration. Transgenic aspen tissue has been prepared and transgenic plants have been regenerated [Devellard et al. (I992) *C.R. Acad. Sci. Ser.* VIE 314:291–298K; Nilsson et al. (1992) *Transgenic Res.* 1:209–220; Tsai et al. (1994) *Plant Cell Rep.* 14:94–97]. Poplars have also been transformed [Wilde et al. (1992) *Plant Physiol.* 98:114–120]. Technology is also available for the manipulation, transformation and regeneration of Gymnosperm plants in the laboratory. For example, U.S. Pat. No. 5,122,466 [Stomp et al. (1992)] describes the ballistic transformation of conifers, with preferred target tissue being meristematic and cotyledon and hypocotyl tissues. U.S. Pat. No. 5,041,382 [Gupta et al. (1991)] describes enrichment of conifer embryonal cells.

Techniques and agents for introducing and selecting for the presence of heterologous DNA in plant-cells and/or tissue are well-known. Genetic markers allowing for the selection of heterologous DNA in plant cells are well-known, e.g., genes carrying resistance to an antibiotic such as kanamycin, hygromycin, gentamycin, or bleomycin. The marker allows for selection of successfully transformed plant cells growing in the medium containing the appropriate antibiotic because they will carry the corresponding resistance gene.

Other techniques for genetically engineering plant cells and/or tissue with an expression cassette comprising an inducible promoter or chimeric promoter fused to a heterologous coding sequence and a transcription termination sequence are to be introduced into the plant cell or tissue by Agrobacterium-mediated transformation, electroporation, microinjection, particle bombardment or other techniques known to the art. The expression cassette advantageously further contains a marker allowing selection of the heterologous DNA in the plant cell, e.g., a gene carrying resistance to an antibiotic such as kanamycin, hygromycin, gentamycin, or bleomycin.

As used herein, the term comprising is intended in a nonlimiting sense.

Compositions and immunogenic preparations comprising a substantially purified protein of interest or an immunogenic peptide having an amino acid sequence derived therefrom and a suitable carrier therefor are provided by the present invention. Alternatively, hydrophilic regions of the protein can be identified by the skilled artisan, and peptide antigens can be synthesized and conjugated to a suitable carrier protein (e.g., bovine serum albumin or keyhole limpet hemocyanin) if needed for use in raising antibody specific for the protein of interest. Immunogenic compositions are those which result in specific antibody production when injected into a human or an animal. These preparations comprise an immunogenic amount of the protein or an immunogenic fragment(s) thereof. Such vaccines may comprise the Msg protein, or in combination with another protein or other immunogen or an epitopic peptide derived therefrom. By immunogenic amount is meant an amount capable of eliciting the production of antibodies directed against the protein of interest in an individual or animal to which the composition has been administered.

Immunogenic carriers can be used to enhance the immunogenicity of protein of interest or peptides derived in sequence therefrom. Such carriers include but are not limited to proteins and polysaccharides, liposomes, and bacterial cells and membranes. Protein carriers may be joined to the protein or peptides derived therefrom to form fusion proteins by recombinant or synthetic means or by chemical coupling. Useful carriers and means of coupling such carriers to polypeptide antigens are known in the art.

The immunogenic compositions and/or vaccines may be formulated by any of the means known in the art. They are typically prepared as injectables, either as liquid solutions or suspensions. Solid forms suitable for solution in, or suspension in, liquid prior to injection may also be prepared. The preparation may also, for example, be emulsified, or the protein(s)/peptide(s) encapsulated in liposomes.

The active immunogenic ingredients are often mixed with excipients or carriers which are pharmaceutically acceptable and compatible with the active ingredient. Suitable excipients include but are not limited to water, saline, dextrose, glycerol, ethanol, or the like and combinations thereof. The concentration of the immunogenic polypeptide in injectable formulations is usually in the range of 0.2 to 5 mg/ml.

In addition, if desired, the immunogenic compositions may contain minor amounts of auxiliary substances such as wetting or emulsifying agents, pH buffering agents, and/or adjuvants which enhance the effectiveness of the immunogenic composition. Examples of adjuvants which may be effective include but are not limited to: aluminum hydroxide; N-acetyl-muramyl-L-threonyl-D-isoglutamine (thr-MDP); N-acetyl-nor-muramyl-L-alanyl-D-isoglutamine (CGP 11637, referred to as nor-MDP); N-acetylmuramyl-L-alanyl-D-isoglutaminyl-L-alanine-2-(1'-2'-dipalmitoyl-sn-glycero-3-hydroxyphosphoryloxy)-ethylamine (CGP 19835A, referred to as MTP-PE); and RIBI, which contains three components extracted from bacteria, monophosphoryl lipid A, trehalose dimycolate and cell wall skeleton (MPL+TDM+CWS) in a 2% squalene/Tween 80 emulsion. The effectiveness of an adjuvant may be determined by measuring the amount of antibodies directed against the immunogen resulting from administration of the immunogen in vaccines which are also comprised of the various adjuvants. Such additional formulations and modes of administration as are known in the art may also be used.

A soybean Msg protein or other protein of interest and/or epitopic fragments or peptides of sequences derived therefrom or from a related protein having a primary structure similar (more than 90% identity) to the particular protein may be formulated into immunogenic compositions as neutral or salt forms. Pharmaceutically acceptable salts include but are not limited to the acid addition salts (formed with free amino groups of the peptide) which are formed with inorganic acids, e.g., hydrochloric acid or phosphoric acids; and organic acids, e.g., acetic, oxalic, tartaric, or maleic acid. Salts formed with the free carboxyl groups may also be derived from inorganic bases, e.g., sodium, potassium, ammonium, calcium, or ferric hydroxides, and organic bases, e.g., isopropylamine, trimethylamine, 2-ethylaminoethanol, histidine, and procaine.

Multiantigenic peptides having amino acid sequences derived from the protein of interest or related protein for use in immunogenic compositions are synthesized as described in Briand et al. [(1992) *J. Immunol. Methods* 156:255–265].

The immunogenic compositions are administered in a manner compatible with the dosage formulation, and in such amount as will be effective for production of antibody specific for the cognate protein. The quantity to be administered, which is generally in the range of about 100 to 1,000 $\mu$g of protein per dose, more generally in the range of about 5 to 500 $\mu$g of protein per dose, depends on the subject to be treated, the capacity of the individuals immune system to synthesize antibodies. Precise amounts of the active ingredient required to be administered may depend on the judgment of the skilled artisan and may be peculiar to each individual, but such a determination is within ordinary skill. Especially for poultry, immunogenic compositions can be administered orally via food or water preparations comprising an effective amount of the protein(s) and/or peptide(s), and these immunogenic compositions may be formulated in liposomes as known to the art.

The immunogenic composition may be given in a single dose or multiple dose schedule. A multiple dose schedule is one in which a primary course of immunization may include 1 to 10 or more separate doses, followed by other doses administered at subsequent time intervals as required to maintain and or reinforce the immune response, e.g., at 1 to 4 months for a second dose, and if needed, a subsequent dose(s) after several months.

Many of the procedures useful for practicing the present invention, whether or not described herein in detail, are well known to those skilled in the art of plant molecular biology. Standard techniques for cloning, DNA isolation, amplification and purification, for enzymatic reactions involving DNA ligase, DNA polymerase, restriction endonucleases and the like, and various separation techniques are those known and commonly employed by those skilled in the art. A number of standard techniques are described in Sambrook et al. (1989) In: *Molecular Cloning*, Second Edition, Cold Spring Harbor Laboratory, Plainview, N.Y.; Maniatis et al. (1982) *Molecular Cloning*, Cold Spring Harbor Laboratory, Plainview, N.Y.; Wu (ed.) (1993) *Meth. Enzymol.* 218, Part I; Wu (ed.) (1979) *Meth Enzymol.* 68; Wu et al. (eds.) (1983) *Meth. Enzymol.* 100 and 101; Grossman and Moldave (eds.) *Meth. Enzymol.* 65; Miller (ed.) (1972) *Experiments in Molecular Genetics*, Cold Spring Harbor Laboratory, Cold Spring Harbor, N.Y.; Old and Primrose (1981) *Principles of Gene Manipulation*, University of California Press, Berkeley; Schleif and Wensink (1982) *Practical Methods in Molecular Biology*; Glover (ed.) (1 985) *DA Cloning* Vol. I and II, IRL Press, Oxford, UK; Hames and Higgins (eds.) (1985) *Nucleic Acid Hybridization*, IRL Press, Oxford, UK; and Setlow and Hollaender (1979) *Genetic Engineering: Principles and Methods*, Vols. 1–4, Plenum Press, New York, Kaufman (1987) in *Genetic Engineering Principles and Methods*, J. K. Setlow, ed., Plenum Press, NY, pp. 155–198; Fitchen et al. (1993) *Annu. Rev. Microbiol.* 47:739–764; Tolstoshev et al. (1993) in *Genomic Research in Molecular Medicine and Virology*, Academic Press. Abbreviations and nomenclature, where employed, are deemed standard in the field and commonly used in professional journals such as those cited herein.

Each reference cited in the present application is incorporated by reference herein to the extent that it is not inconsistent with the present disclosure.

The following examples are provided for illustrative purposes, and are not intended to limit the scope of the invention as claimed herein. Any variations in the exempli-

EXAMPLES

Example 1

DNA and RNA Methods

Standard laboratory procedures were used for DNA and RNA extractions, blotting, DNA probe labeling, PCR and restriction enzyme digestion of DNA as described [Sambrook et al. (1989) In: *Molecular Cloning: A Laboratory Manual.* 2$^{nd}$ Edn., Cold Spring Harbor Laboratory Press, Cold Spring Harbor, N.Y.; Lindstrom et al. (1990) *Dev. Genet.* 11:160–167; Cho et al. (1995) *Plant Mol. Biol. Rep.* 13:255–269; Todd and Vodkin (1996) *Plant Cell* 8:687–699]. Sequencing and primer syntheses were performed using commercially available automated equipment by the Genetic Engineering Facility at the Biotechnology Center, University of Illinois. The DNA sequence was analyzed using the functions at the BCM Search Launcher on the Internet at (http://gc.bcm.tmc.edu:8088/search-launcher.html). The putative amino acid sequence was analyzed by using Proteomics tools at the ExPASy web site at (http://expasy.hcuge.ch/).

fied sequences and methods which occur to the skilled artisan are intended to fall within the scope of the present invention.

Example 2

Construction and Screening of the cDNA Library

A cDNA library was constructed using the Superscript Lambda system kit (BRL, Life Technologies Inc., Gaithersburg, Md.). About 1.8 µg of mRNA from young soybean pods (UC75, an isoline of the cultivar Clark), isolated by the PolyATtract mRNA isolation kit (Promega, Madison, Wis.), was used to construct the cDNA library according to the manufacturer's instructions. The size fractionated cDNAs were ligated to λZipLox, Not I -Sal I arms, packaged in vitro using a λ-packaging system (BRL) and used to infect *E. coli* Y1090(ZL) cells.

Bacteriophage clones containing cDNA inserts were identified by PCR. Primary phage plaques were picked from the library and resuspended in 500 µl of SM buffer (100 mM NaCl, 8 mM MgSO$_4$, 50 mM Tris-HCl pH 7.5, 0.01% gelatin) and 20 µl of chloroform. Aliquots of individual phage stocks (5 µl volume) were subjected to quick freeze thaw in liquid nitrogen for a total of three times. These DNA samples were then amplified by PCR using M13 forward and reverse primers. Following amplification, the PCR products were electrophoresed through a 0.7% agarose gel in 1×TA (40 mM Tris Acetate, pH 7.8) [Sambrook et al. (1989) supra]. After staining the gels with ethidium bromide the fragments of interest were cut out and purified by passing through a 0.2 µm syringe filter (Gelman Sciences, Ann Arbor, Mich.) [Lu et al. (1994) *BioTechniques* 16:400–402].

The syringe-purified PCR products were used as probes for Northern blots. Probes were prepared by random primer reaction and labeled with $^{32}$P-dATP as described [Feinberg and Vogelstein (1982) *Anal. Biochem.* 132:6–13]. Total RNA from soybean seed coats, immature cotyledons, leaves, stems, roots, young and old pods along with appropriate markers were electrophoresed on gels and blotted onto supported nitrocellulose membranes (Optitran®, Schleicher & Schuell, Keene, N.H.). The RNA on the membranes were hybridized to the labeled probe at 68° C. and detected on X-ray film (HyperfilmTM MP, Amersham LifeScience, Buckinghamshire, England).

The cDNA library was also screened using the radioactively labeled PCR product of the VS-107 cDNA clone as a probe. Three plates with an average of 40,000 pfu per plate were screened using *E. coli* Y1090 as a host. The total number of positive plaques was counted, and 12 positives were isolated by secondary and tertiary screening. The vectors were in vivo excised into plasmids pZLVS107:1-pZLVS107:12 by mixing 25 µl of phage solution with 100 µl of *E. coli* DH10B(ZIP) cells, incubated at room temperature and plated on LB plates containing 10 mM MgCl$_2$ and 100 µg/ml ampicillin. Plasmid DNA was extracted using the QIAprep Spin Miniprep kit (Qiagen Inc., Valencia, Calif.).

Example 3

Screening a Genomic Library

A soybean genomic library in the Lambda Fix®II Vector (Stratagene, La Jolla, Calif.) was screened using the PCR product of the god specific VS-107 cDNA clone as a probe and the *E. coli* host strain XL1-Blue MRA(P2). The library was made from DNA of *Glycine max* cv Williams 82 partially digested with Sau 3A I. The host bacteria were grown, infected and plated as described in the library instruction manual. An average of 45,000 pfus were plated on each of 12 petri plates (size 150×15 mm, Fisherbrand® cat. #08-757-14) making the total number of phages screened approx. 540,000. Plaque lifts were performed using 0.45 micron, 137 mm NitroPure, supported nitrocellulose membranes (Micron Separations Inc., Westboro, Mass.) and following the procedure in the library instruction manual. The probe was radiolabeled and hybridized to the DNA on the membranes at 68° C. Positive clones were detected on X-ray film. After the tertiary screening, the isolated phage plaques were diluted and stored as described for the cDNA clones.

Example 4

Mapping, Subcloning and Sequencing of Genomic Lambda Clones

The genomic lambda clones were cultured (500 ml) as described [Sambrook et al. (1989) supra], and DNA was extracted using the Qiagen Lambda Maxi Kit (Qiagen, Valencia, Calif.). The lambda DNA was restriction digested and maps were combined of results from x-ray-RFLP data and from the FLASH fluorescent kit data (Stratagene, La Jolla, Calif.). The plasmid DNA (pGEM3zf+, Promega, Madison, Wis.) and the 16 kb lambda Msgb DNA were double digested with Sal I and Eco RI. Two fragments resulted from the lambda Msgb, a 3.2 kb fragment containing the coding region (pMsg250) and a 6.3 kb fragment containing the 5'-flanking (promoter) region (pMsg251). The digested DNAs were purified by QIAquick PCR Purification kit (Silica gel membrane, Qiagen, Valencia, Calif.) and then ligated at 12° C. overnight. The ligation products were transformed into *E. coli* DH5 using standard procedures [Sambrook et al. (1989) supra] and selected on LB plates containing ampicillin (50 µg/ml). Positive clones were identified following plasmid mini-prep [Zhou et al. (1990) *BioTechniques* 8:172–173] and restriction enzyme (EcoRI, HindIII, HincII, SalI). analysis. See SEQ ID NO:1 and SEQ ID NO:2 for nucleotide and deduced amino acid sequence information and GenBank Accession No. AJ239127.

Example 5

Constructs for Promoter Analysis

Primers were designed to anneal at –2256 bp (Msg1F), –1684 bp (Msg4F), –1220 bp (Msg5F), –651 bp (Msg8F), −634 bp (Msg2Ratg and Msg3R), 0 bp (Msg6Ratg) and +3 bp (Msg7R) relative to the start codon (FIG. 3). A HindIII restriction enzyme site was included as an overhang in the 5'-end primers (Msg1F, Msg4F, Msg5F and Msg8F) and a Bam HI site was included in the 3'-end primers (Msg2Ratg, Msg3R, Msg6Ratg and Msg7R). Two sets of deletion fragments were made using either Msg2Ratg/Msg3R (A92atg-F219 constructs) primers or Msg6Ratg/Msg7R (G305atg-N353 constructs) as the reverse primer. The forward primers used to obtain 5'-deletions were the Msg1F for the A92atg, B103, G305atg, H358 constructs, Msg4F for the C211atg, D162, I372atg, J312 constructs, Msg5F for the E178atg, F219, K340atg, L318 constructs and finally the Msg8F for the M347atg and N353 constructs. The resulting constructs, name and size can be seen in FIG. 6. For the A92atg-F219 constructs the pMsg251 subclone was used as a PCR template and for the G305atg-N353 constructs the lambda Msg2 DNA was used. The PCR product was purified using the QIAquick PCR Purification kit (Qiagen) and the fragments and the recipient plasmid pBI101 [Bevan, M. W. (1984) supra; Jefferson et al. (1987) supra] were double digested with Bam HI and HindIII. The fragments and linear plasmid were again purified with the QIAquick PCR kit and then ligated at 12° C. overnight. The ligation products were transformed into E. coli DH5. Plasmid DNA was extracted using Qiagen Plasmid Maxi kit (Qiagen). Restriction enzyme digests using Bam HI and HindIII, and PCR using the cloning primers, confirmed the desired transformants. The plasmid DNAs containing the inserts were used for particle bombardment of soybean and green bean pods and for freeze thaw transformation of Agrobacterium tumefaciens [Holsters et al. .(1978) *Mol. Gen. Genet.* 163:181–187].

The intron and 3'UTR-constructs were made in the pBI101 backbone. In FIG. 8 an overview of all the Msg constructs is shown. FIG. 9 shows the T-DNA region of the full Msg construct pBMGIU44.

Primers were designed to yield an intron fragment with Sna BI overhangs to be cloned into the Sna BI site in the uidA coding sequence. The intron was first amplified by PCR, purified using the QIAquick PCR Purification kit (Qiagen, Valencia, Calif.) and cloned into the pGEMT-Easy vector (Promega, Madison, Wis.). Sna BI-restricted plasmid was run on a 1% low melting temperature agarose gel (SeaPrep, FMC BioProducts, Rockland, Me.). The intron band was cut out and purified using the QIAquick gel extraction kit (Qiagen, Valencia, Calif.) and then ligated to the Sna BI restricted vectors pBMMU12 and pBMGU1. The 3'UTR was amplified by PCR using primers with Eco RI and Sst I overhangs and subsequently digested with those enzymes. The digested fragment was purified using the Qiagen PCR purification kit and cloned into the Eco RI/Sst I restricted plant transformation vector pBI101. The 3'UTR clones were screened by restriction endonuclease digestion with Hin cII because the Msg 3'UTR but not the native nosT contains a Hin cII site. The constructs that contain both the Msg 3'UTR and either of M and G 5'regions were made by first inserting the 3'UTR into pBI101, and then the M or G fragment. The M or G fragments were amplified by PCR, digested with Hin dIII and Bam HI and subsequently cloned into the pGEM3zf+ plasmid. They were excised using Hin dIII and Sma I and electrophoresed on a 1% SeaPrep low melting agarose gel. The bands were excised, melted at 60° C. and then ligated directly into the Hin dIII-Sma I digested transformation vector using the Rapid DNA Ligation Kit (Roche Molecular Biochemicals, Indianapolis, Ind.). The constructs were transformed into Agrobacterium with the freeze-thaw method (Holsters et al., 1978). All Agrobacterium strains carrying these constructs were tested for GUS activity.

The Agrobacterium infiltration procedure was adapted from Bechtold et al., 1993 and Clough and Bent, 1998. *Arabidopsis thaliana* ecotype Columbia was sown in pots covered with window nylon mesh and cultured in 18–24 h light until bolting. The main shoot was cut down to promote side shoots forming. The transformation procedure was performed when unopened flower buds were numerous (about 2–5 days after the main shoot cutting). *Agrobacterium tumefaciens*, strain GV3101 (pMP90) (Koncz and Schell, 1986) transformed with the promoter constructs were grown to a high density (O.D.600>1.2) in YT medium containing kanamycin (0.05 mg/ml). The cells were harvested by centrifugation at 5500×g and resuspended in infiltration medium containing ½×MS salts and Gamborg's vitamins, 44 nM benzylaminopurine, 5% sugar and 0.005% Silwet L-77, pH 6.3. A beaker containing the infiltration media and the suspended bacteria was placed in a desiccator and the potted, bolting plants were placed inverted in it. Vacuum was applied briefly. The pots were returned to the 18–24 h light culture condition and maintained until siliques were dried and opened and the seeds ready to harvest. The transformed seeds were selected on 1/2×MS plates containing kanamycin (50 µg/ml). Histochemical GUS assays were performed as described (Stomp, 1992), on flowering plants. Plant material was immersed in GUS assay buffer (50 mM $NaPO_4$, 0.5 mM $K_3Fe(CN)_6$, 0.5 mM $K_4Fe(CN)_6$, 10 mM $Na_2EDTA$, 1 mM X-Gluc, and 0.1% Triton X-100, pH 7) and incubated overnight at 37° C.

The *Agrobacterium tumefaciens* strain GV3101 transformed with the pBMG3 05, pBMM347, pBMGU1, pBMGIU44, pBMMU12, pBMMInU 11, pBMMIU32, pBMU2, pBI101 and pBI121 constructs were assayed for GUS activity. Bacteria from the −70° C. stocks were plated on YT kan 50 plates and grown for two days at 28° C. Bacteria were scraped up with a toothpick and suspended in 250 µl GUS assay buffer and observed after an hour and then incubated overnight at 37° C. and observed again.

Example 6

Agrobacterium Infiltration/Floral Dipping/in planta Transformation

The Agrobacterium infiltration procedure was adapted from [Bechtold et al. (1993) supra] and [Clough and Bent (1998) supra]. *Arabidopsis thaliana* ecotype Columbia was sown in pots covered with window nylon mesh and cultured in 18–24 h light until bolting. The main shoot was cut down to promote side shoots forming. The transformation procedure was performed when unopened flower buds were numerous (about 2–5 days after the main shoot cutting). *Agrobacterium tumefaciens*, strain GV3101 (pMP90) [Koncz and Schell (1986) supra] transformed with the Msg-promoter:GUS constructs was grown to a high density ($OD_{600}$>1.2) in YT medium containing kanamycin (0.05 mg/ml). The cells were harvested by centrifugation at 5500×g and resuspended in infiltration medium containing ½× MS salts and Gamborg's vitamins, 44 nM benzylaminopurine, 5% sugar and 0.005% Silwet L-77, pH 6.3. A beaker containing the infiltration media and the suspended bacteria was placed in a desiccator and the potted, bolting plants were placed inverted in it. Vacuum was applied briefly. The pots were returned to the 18–24 h light culture condition and maintained until siliques were dried and opened and the seeds ready to harvest. The transformed seeds were selected on ½×MS plates containing kanamycin (50 μg/ml). Histochemical GUS assays were performed on flowering plants and as described in [Jefferson, R. A. (1987) *Plant Mol. Biol. Rep.* 5:387–405] and modified as in [Stomp, A.-M. (1992) In: *GUS Protocols. Using the GUS Gene as a Reporter of Gene Expression*, Gallagher S. R. (Ed), Academic Press Inc., San Diego, Calif. pp.103–113]. The plant tissue was immersed in GUS-assay buffer containing 5-bromo-4-chloro-3-indolyl-β-D-glucuronic acid (X-gluc) (Jersey Lab Supply, Livingston, N.J.) and incubated at 37° C. overnight.

Example 7

Particle Bombardment

Pods and leaves of field grown soybeans Glycine max (L.) Merr. and pods of green bean *Phaseolus vulgaris* (L.) from the grocery store were collected and surface sterilized in a 50% bleach, 0.1% Tween 20 solution. After the seeds and seed coats were removed, the inside of the pods were shot using gold particles (o 1 μm with 2.5 μg of plasmid DNA/ shot) with a BioRad Biolistic PDS-1000/He gun (DuPont) [Klein et al. (1987) supra] or a particle inflow gun [Finer et al. (1992) supra]. As a positive control for transient GUS reporter gene expression, the plasmid pZA300 encoding a CaMV35S-uidA construct was used. The pZA300 plasmid was a gift from J. H. Zhou and A. G. Atherly, Iowa State University. Soybean cotyledons, seed coats and leaves were also bombarded with the same constructs. Two days after the bombardment, a histochemical GUS assay was performed as described above.

Example 8

Pathogen Induction Study

Arabidopsis transgenic for pBMG305atg (T3 generation), pBMM347atg (T3 generation), pBI101 (T2 generation) and pBI121 (T2 generation) were selected on ½ MS with Gamborg's vitamins (Sigma, St Louis, Mo.) plates containing kanamycin (50 μg/ml). Wild-type Columbia plants were grown on ½ MS (with Gamborg's vitamins) without selection. Plants were transferred to soil in 2 inch×2 inch pots and grown until bolting. The soil was contained by taping around the plant. The Pseudomonas strains were maintained on A.B. minimal medium plates ($NH_4Cl$, 1 g/l; $MgSO_4$-$7H_2O$, 0.3 g/l; HCl, 0.15 g/l; $CaCl_2$, 0.01 g/l; and $FeSO_4$-$7H_2O$, 1.5 mg/l; in a phosphate buffer ($K_2HPO_4$, 3 g/l; $NaH_2PO_4$, 1 g/l), 0.2% glucose, pH 7.

Two pathogenic strains of pseudomonads were introduced using the pathogen vacuum infiltration technique [Yu et al. (1998) *Proc. Natl. Acad. Sci. USA* 95, 7819–7824]. The pathogens used were *Pseudomonas syringae* DC3000 (pVS288, avr+) and (pVSphi6l, avr−) [Kunkel et al. (1993) Plant Cell 5, 865–875, Yu et al. (1993) Molec. Plant Microbe Interact 6, 434–443], *P. fluorescens* (strain 1855–344, kindly provided by P. Oger from S. Farrand's lab) [Hwang and Farrand (1994) Appl. Environ. Microbiol. 60, 913–920] and the negative control was 10 mM $MgCl_2$ without bacteria. The pathogens were grown on NYGA kan 25/rif 100 plates (per liter: 5 g Bacto-peptone, 3 g yeast extract, 20 ml glycerol, 15 g Bacto-agar, 25 mg kanamycin, 100 mg rifampicin, pH7.0) for two days. Bacteria were scraped from the plates and resuspended in 10 mM $MgCl_2$ to $OD_{600}$ and diluted 50 μl to 500 ml of 10 mM $MgCl_2$, a final infiltration concentration of $2-5\times10^4$ cfu/ml. Three plants of each transgenic line were infiltrated with each bacterial strain.

In the determination of the hypersensitive response (HR), the pathogens used were *Pseudomonas syringae* race4 (pVS288, avr+) and (pVSphi61, avr−) and the negative control was 10 mM $MgCl_2$ without bacteria. One colony of each bacterial strain was used to inoculate 5 ml YT kan 25 (per liter: 10 g Bacto-tryptone, 5 g yeast extract, 5 g NaCl, 25 mg kanamycin, pH 7.3). One ml of the overnight culture was used to inoculate 250 ml YT kan 25 which was incubated at 28° C. with shaking for 24 hours, centrifuged at 3000 rpm for 10 min at 4° C. in a JA-14 rotor. The pellet was resuspended and diluted to $OD_{600}=0.23$. The bacterial suspension was aspirated into a 1 cc syringe. The back side of the leaf to be treated was gently scratched with the syringe and then, by pressing semi hard and pushing the plunger, the bacterial suspension was infiltrated into the leaf. One half of an Arabidopsis rosette leaf was treated while the other was left alone. Three leaves per plant were treated. Two plants of each line were hand inoculated with avr+ and one plant each with avr−. A histochemical GUS assay was performed 24 hours later as described above.

To fix and dehydrate tissue for whole mount in situ hybridization, the tissues were collected from the soybean line Williams 82 grown in the greenhouse or germinated in the laboratory. In the former case soybean plants were sown in soybean-mix soil (1:1:1-Soil:Perlite:Torpedo Sand, Plant Care Facility, University of Illinois, Champaign, Ill.) and in the latter case soybean seeds were placed in a row on autoclaved wetted paper which subsequently was rolled into a roll and attached with a rubber band. The rolls were put in a glass beaker with deionized autoclaved water, left on a growth shelf and watered when dry. Tissues (pods, stem, nodes) were cut into suitable pieces and immediately slipped into fixation buffer consisting of 3.7% formaldehyde, 50% ethanol and 5% acetic acid and left on gentle shaking (80 rpm) for 3 h [Gijzen et al. (1999) *Plant Mol. Biol.* 41, 57–63; Gijzen et al. (1999)Plant Physiol. 120, 951–959] or alternatively into fixation buffer consisting of 0.08 M EGTA (ethylene glycol bis(β-aminoethyl ether) N,N,N',N'-tetraacetic acid), 5% formaldehyde, 10% DMSO (dimethyl sulfoxide) in phosphate buffered saline with Tween-20 (PBT: 120 mM NaCl, 7 mM $Na_2HPO_4$, 3 mM $NaH_2PO_4$, 2.7 mM HCL, 0.1% Tween-20, pH 7.4), pH 7.4 for 30 min [de Almeida Engler et al. (1994) Plant Mol. Biol. Reprtr.12, 321–331]. After fixation, the tissues were dehydrated following the protocol in de Almeida Engler et al, 1994: twice subjected to absolute methanol and four times in absolute ethanol, 5 min each time. The fixed tissues were stored in absolute ethanol at −20° C.

To synthesize probes for in situ hybridization, the excised plasmid pZLVS107 was linearized for 5 hours at 37° C. with Sal I (anti-sense probe with SP6 RNA polymerase) and with Not I (sense probe with T7 RNA polymerase). Subsequently the linear templates were purified using the QIAquick PCR purification kit (Qiagen, Valencia, Calif.). The RNA probes were prepared in vitro using the DIG RNA Labeling Kit (SP6/T7) (formerly Genius 4) (Roche Molecular Biochemicals, Indianapolis, Ind.). The purified linear plasmid (lug) was incubated for 3 h at 37° C. with 4 µl of NTP (nucleotide triphosphate) labeling mix, 4 µl of transcription buffer, 2 µl of RNase inhibitor, 20 µl of diethyl pyrocarbonate (DEPC)-treated water and 4 µl of polymerase. The samples were treated with 2 µl of DNase for 15 min at 37° C. to eliminate the DNA template. Small fractions of the samples were run on a denaturing RNA gel to confirm the oligonucleotide size. After the DNase treatment, the probes were ethanol precipitated and redissolved in 100 µl alkaline hydrolysis buffer (40 mM $NaHCO_3$, 60 mM $Na_2CO_3$, pH 10.2). The RNA probes were digested for 45 min at. 60° C. to an average length of 150 nucleotides by the second method of controlled alkaline hydrolysis [Cox et al. (1984) Devel. Biol. 101, 485–502]. To calculate the incubation time the following equation was used:

$$t=(L_0-L_f)/kL_0L_f$$

where t is the incubation time, $L_0$ is the initial fragment length in kb, $L_f$ is the final fragment length in kb, and k is the rate constant for hydrolysis which is approximately 0.11 $kb^{-1}$ min [(Cox et al. (1984) supra]. To neutralize and precipitate the RNA fragments, 10 µl of 3M sodium acetate (to a final concentration of 0.1 M), 1.5 µl of glacial acetic acid (to a final concentration of 0.5% v/v) and 200 µl (2/3 volumes of final concentration) of absolute ethanol, were added. The probes were placed in −70° C. overnight. The probes were pelleted by centrifugation at 4° C. for 25 min at 11,000 rpm in a Biofuge B (American Scientific Products), washed with 80% ethanol (centrifuged 3 min), dried for 3 min in a savant speed vac (no heat), then redissolved in 20 µl of DEPC treated TE buffer (10 mM Tris, 1mM EDTA, pH7.5).

To obtain plant powder for use in immunoblot experiments, modifications to the original protocol of de Almeida Engler et al. [1994, supra] were made essentially as follows. Fresh and fixed tissues were frozen in liquid nitrogen and then dried on a lyophilizer for two days. Equal amounts of fixed and fresh tissue were mixed after being homogenized to a powder by Fastprep-grinding in 2 ml microfuge tubes with 10 glass beads in each. The beads were removed and the plant powder was stored at 4° C. in a plastic food container with indicating Drierite (97% $CaSo_4$ and 3% $CoCl_2$ (W.A. Hammond Drierite Company Ltd.).

Thirty mg of the dry plant powder was suspended in 400 µl of PBT containing 2% bovine serum albumin (fraction V) and to this, 20 µl of anti-DIG alkaline phosphatase Fab fragments from sheep (Roche Molecular Biochemicals, Indianapolis, Ind.) was added. The mix was incubated in darkness at room temperature for 24 h and subsequently cleared by centrifugation for 3 min at 10,000×g.

The dehydrated tissues were transferred to 12 ml orange capped tubes and rinsed twice for 5 min in absolute ethanol and once in a 1:1 ethanol-xylene mixture for 30 min, followed by washing twice in absolute ethanol and twice in absolute methanol for 5 min each. Then a wash for 10 min in 1:1 methanol:phosphate-buffered saline (PBT) mix followed and post-fixation in PBT with 5% formaldehyde for 30 min. The samples were washed three times in PBT, 5 min each, and then incubated for 10–15 min in room temperature in PBT with 40 µg/ml of proteinase K (60 µl of a 13.3 mg/ml stock solution to 20 ml of PBT). To stop the reaction, the samples were washed in PBT with 0.2% glycine for 5 min and twice in PBT. Post-fixation was again carried out for 30 min in PBT with 5% formaldehyde and followed by four rinses in PBT. The samples were transferred to glass scintillation vials in which they were equilibrated in 1:1 PBT:hybridization solution (HS) for 5 min, rinsed twice in HS, then prehybridized for 2 h at 60° C. HS contains 50% formamide, 5×SSC (1×SSC: 150 mM NaCl, 15 mM sodium citrate, pH 7.0), 50 µg/ml heparin.

The DIG-labeled RNA probe and the calf thymus DNA were denatured for 5 min in 93° C. and added to 5 ml of hybridization solution to final concentrations of 1–3 µg/ml and 100 µg/ml respectively. The calf thymus substitutes the salmon sperm that the original protocol calls for [de Almeida Engler et al. (1994) supra]. The vials were wrapped in wetted paper towels and placed in 50 ml orange capped tubes which were then placed in a hybridization oven for 20 h at 60° C. with constant rotation.

The tissue was washed for 30 min twice in fresh HS at 55° C. and once for 60 min in 1:1 HS:NTE at room temperature. This was followed by a wash in NTE (500 mM NaCl, 10 mM Tris-HCl, pH 7.5, 1 mM EDTA) at room temperature for 60 min, a brief rinse in NTE and then a 45 min incubation at 37° C. in NTE with 40 µg/ml of RNase A. The samples were washed in NTE at 37° C. for 15 min and five times 15 min with NTE at room temperature. Equilibration for 20 min in 1:1 NTE:PBT was followed by a rinse in PBT and incubation with BS (blocking solution: 2% bovine serum albumin Fraction V, in PBT) containing 5% of normal sheep serum for 30 min.

The BS was replaced by freshly made solution and 60 µl of the preabsorbed antibody (dilution 1:2000) was added. The samples were incubated overnight at 4° C., then incubated in fresh BS for 10 min and washed four times 15 min with PBT.

The samples were equilibrated in staining buffer (SB: 100 mM NaCl, 50 mM $MgCl_2$, 100 mM Tris-HCl, pH 9.5, 0.1% Tween-20) twice for 5 min and then 2 ml of fresh SB containing 1 mM of levamisole (inhibitor of endogenous alkaline phosphatase), 4.5 µl of NBT (75 mg/ml nitrobluetetrazolium in 70% v/v $H_2O$/dimethylformamide) and 3.5 µl of BCIP (50 mg/ml of 5-bromo-4-chloro-3-indolyl phosphate in water) were added. The vials were wrapped in aluminum foil to allow the reaction to succeed in the dark for 60 min. The reaction was stopped by adding 1 ml of stain stop buffer (SSB: 20 mM EDTA in PBT) and then the samples were rinsed twice in SSB.

Phloroglucinol (Sigma, St. Louis, Mo.) in aqueous solution (0.1 g to 10 ml $H_2O$) was added in drops simultaneously with drops of 6 M HCl [Chamberlain (1932) Methods in Plant Histology, $5^{th}$ Ed., University of Chicago Press, Chicago, Ill.] onto soybean pods that had been subjected to in situ hybridization.

Table 1. Nucleotide Sequence and Deduced Amino Acid Sequence of the Soybean Msg Gene (SEQ ID NO:1 and SEQ ID NO:2)

TABLE 1

Nucleotide Sequence and Deduced Amino Acid Sequence of the Soybean Msg Gene (SEQ ID NO:1 and SEQ ID NO:2)

```
-2274  TCCATTGTGGAAACCCGACGAGTTTAATTCACAAGCACAACGAGTTAAAATGATTTTGAAAATAATTGAGTAGTTGTGTATTGCATAAGTTCATAAGTAA   100
              Msg1F
-2174  AGTGTGTGATTCATGAAATGTGATGACATGTTAAATTGATTATACTATTGTGATTGAGATCGAGTGTATGTGATAAATTGAGTATGTACGTGATTG        200
-2074  TGATGTGTTTGCATTGAGTTATGAACATGAATTGTACAATCATATGACTTTAAAGACCCTTAAGGGCGGCGAGTTAATTATAAGACCCTTAAAGGGCG     300
-1974  GTGAGTTAATTATAAGACCCTTTAAGTGCGGTGAGTTAATTTGTACAGTTCATATGAAGAGCCCTTTAAGGGTGACGAGTTAAA                    400
-1874  ACTATTTTTGAGAATAATTGAGGACTCGTGTGTTTGTACAGTTCATATGATAGAGTTTGTGTCTAAAATGTTTCTGAGTTGGACCTGAATCAGGAGGG    500
-1774  AGAGGCCCCGACGGACTCTTCGGAGTGTAGGCCCTTGGGGGTCACCCGATTGAGTGTTTCTTTAAGCCTATGTGATCCCATATGATTGGAGCATTCTCG   600
                                                                                                    Msg4F
-1674  TAAAACACTGTGATCCTGACTGGTCTCCCCTATGATAATTACCTACTAGTGAGAGTTACTTACTAGTGTGTTGTCTGTCATGTACTCCTAGGCGC        700
-1574  CCGACGAGATTTTTCACTGACATGGTACCACATTGCATATAGACTTGAGTTTTAGCATAACTGTTGCATACGCTTGCTAATTGTTTATCATGAAATTGAT   800
                  KpnI
-1474  GTGTTATTATGTCTTGATCAGAGATGTGTGATTCTTGTATATTGTGATGGATGATTGAAAGTGCAATTTTGAATGACAAAGTGG                   900
-1374  TGAAATAATGTGAGCTATGCTAAGTAGATTGTATTTGGCTACTATATGTTAATCTCGTTCTCCTAGTAGTTAGGAATGTGATAACTCACTCTCGGTTTG   1000
-1274  CTGGTATTTGAAATCCTGTGATGATCCTGAATTTGTATTCAAGGAGCGAGATGACTAGAACTGCTTAAGGAATATTGCTGAAATATTGTCGAAGGATGTCGGGAC  1100
                                                                              Msg5F
-1174  ACAATGTCTCGATAGGATGTGACATTGGATAATAAGTTTTATATTAATTTATCATGTTAATCTATTTTATTTACCTCACTGATTTAACAAAATATTT     1200
-1074  TTATAAATTTGTGACGGACTTATTTTGAGCCGAATATGTTTTTAATTAGTTTTAATGATAATAGTGCAGTGGATGTGAACCTTTAGCCATGTGAATTT    1300
-974   GTTTTCCAATATTTTATTTTATATATATATTTATATACATATATGTCGGGGTAGAGGATGTCACATCTTCACTCCAAACATCTCATTAATATCAATCATAT   1400
-874   TCTTCTTGATTATCATATCTAGCCACCCCTTTATCTCATTTCTTCACTGAGTGTCCAATAATTTTTAGTGTCTACCAATCCATTTTTATATATAGATA    1500
                                                                      AccI
-774   TATATTGTTGATTATGGTATTGATATAAATAATTACTATTGAAAGTAACGATTAATATATTCATTAGAAATCGTGAGCACACTTAAGGTAAGTACTCTCCT  1600
              Msg2Ratg/Msg3R
-674   TTCATTATGATTTATTTATATCCAAAGTCAGAATTCAAATTCTATATCGCTTGCTTATTAAAACACAAACTTATTTTTTACATATATATTCACTGAAAA   1700
                                 Msg8FEcoRI
-574   TAAACATAAAAATGACACTTAATAATAATGTTTCTTTCTTTATTTTTGAAATACCAAAACTTTGTTTCATATGTAAAGGGAAAAGGAATAATACTATTA   1800
-474   AGCTACACCATGAAATCAAACAAAAAATTATCATTGGAATGATATATAAAATCAATAAAATTTATCCACATATAATTTATGATTTCATACACAATAG    1900
-374   GATAATAGTTTACACTTTCATTGCAACAGTATATAATGACATATTTATTCTACGTTGTGTGCCCACTTATTCTTAATAATAGTAGAAGAGGAAAG      2000
-274   GGAAATTCAATATTTACTTCTTCCATTTCCCTTTACGCCGTTCATCATCATTTTTCAACTTTGAAAGTTTTTTTGTCTTTTTTCAAAAGAAATTCTATT  2100
```

TABLE 1-continued

Nucleotide Sequence and Deduced Amino Acid Sequence of the Soybean Msg Gene (SEQ ID NO:1 and SEQ ID NO:2)

```
-174  GTATTAATACATTGAGAAAAGAAGAACAAAGATAAAACATGTTAAGTTTAAGATGTGAAAAACCACGACCATTTGAGCCTCTATATAGGTGTCTCGTA       2200
                                                                  Msg6Ratg/Msg7R -74  TGCTCAAACATGACAAGCCAGTGATAGTTGCTTTCAGATAACTGATAGTTGTGTGCAATTATTTGAATTCAAGAATGTCTCAACCCGACTCGTTGGTGC       2300
                                                                   EcoRI     M   S   Q   P   D   S   L   V   A +27  TGAGATTGAGGTGAAAACCTCTGCAGATCACTTTTACGACACCTTGAAGGGTAAGAAGACATCGTATTCATGATGTTGCCCCTCATCATATCCATAAG       2400
       E   I   E   V   K   T   S   A   D   H   F   Y   D   T   L   K   G   K   K   Q   H   R   I   H   D   V   A   P   H   I   H   K +127  GTGGAAGTTCATGAAGGTGAGTGGGATAAATCTGGCAATATCAAGGTGCTTACATTCGCTGATGGTAAGTAAACTTAATAACAATTCACAGCTATA        2500
       V   E   V   H   E   G   E   W   D   K   S   G   N   I   K   V   L   T   F   A   D +227  TATCTTCTATTCCATATGTTGTTATGATTAAGTTATCATTGTTATTATTGTTGATATATTATGTAGGGACACTGTTGAGACCTTAAAGGAGAGAGT       2600
                                                                                G   D   T   V   E   T   L   E   R   V +327  TGATTTGATGATGAAAACAAGAAGAATAACCTACCACCATATTGGAAGGTGTCATGTTGAAGTACTATAAGAGTACAAGGTTATCGTTCATGTTTTACCA    2700

D   F   D   D   E   N   K   K   I   T   Y   T   I   L   E   G   V   M   L   K   Y   Y   K   S   Y   K   V   I   H   V   L   P

+427  AAAGGTGATGAGCACAGCCTTGTGAAGTGGACTTTCTTGTATGAGAAGGTGGATCACACTGCCCCTGAGCCAACCAAGTACACAAAGATTGGTGGTTAAAC      2800
       K   G   D   E   H   S   L   V   K   W   T   F   L   Y   E   K   V   D   H   T   A   P   E   P   T   K   Y   K   D   L   V   V   K

+527  TCACCAAGAACGTGGAGGCTCATCTTGTTGAGGCTCGTTAAAATGATCCCTAAGTTCACGCTAAATAAAGTTGTGATGTGTGTGTTGCATGT          2900
       L   T   K   N   V   E   A   H   L   V   E   A   R   stop        polyA signal +627  GGGCCCCTTGGTTAATTATCAGCCATTAGTTTGCTTTAAATTGCCGTGCGTAATATGTTGTTGGTTAACTTGTTAAAAATATTGGTTCTCAACCATAAGT    3000
                                                                                                 HindIII +727  TGTGTAAATGTGTTGTTGGTTTATTCAAAATATTGGCCGGGGATCACAGGAGGGCTACATGCCTTTGTATGTCTGTGATTTGTAATCTTCGACCAGCTAT    3100

+827  TGATTAATTGATGTTAAGGGGGATTTTATCCTTGTTGTCTCAAACATTTTTGCCAAATACTTTTTGATAACTAGAAGGTTTGTTGGATAGCCGGTTTTCTTC  3200

+927  ATTTGGGAAGCTTACAGGCATGCATTGGCTAAAACCAGAAGAAATTAAATGTCAAAATGCTTCCACAAAAGTTGTTTAATTTAAATTAAACACTTGAATA      3300
       HindIII    SphI +1027 TGTTTTAATCCCTGAAAAATTTACAGATCTTGCATTTGATATTTAATAATTTCTTTCTTAACTTTTGATTCCTGAAAAATTATTTTATATTTGATTCTTG    3400
```

TABLE 2A

Primers for cloning flanking regions of Msg

| Primer Name | # of nt | Sequence (5'-3') | AT % | Primer annealing location | Position | Comments |
|---|---|---|---|---|---|---|
| MSG 1F (SEQ ID NO:8) | 36 | 5'[CCCAAGCTTGGG]CGAG TTTAATCACAAGCACAAC GA3' | 50% | 5' end of Msg P. 2.3 kb from atg | 5'-2256 -> -2234 3' | Used for cloning Msg promoter. Hind III bracketed |
| MSG4F (SEQ ID NO:9) | 33 | 5'[CCCAAGCTTGGG]AGCA TTCTCGTAAAACACTGT3' | 52% | 5' end of Msg P. 1.7 kb from atg | 5'-1684 -> -1663 3' | Used for cloning Msg promoter. Hind III bracketed |
| MSG 5F (SEQ ID NO:10) | 34 | 5'[CCCAAGCTTGGG]CTAG ATGAACTGCTTTAAGGAA 3' | 53% | 5' end of Msg P. 1.2 kb from atg | 5'-1220 -> -1199 3' | Used for cloning Msg promoter. Hind III bracketed |
| MSG 8F (SEQ ID NO:11) | 33 | 5'[CCCAAGCTTGGG]CCAA AGTCAGAATTCAAATTC3' | 55% | 5' end of Msg P. 0.6 kb from atg | 5'-652 -> -631 3' | Used for cloning Msg promoter. Hind III bracketed |
| MSG2RatgR (SEQ ID NO:12) | 34 | 5'[CGCGGATCCGCG]CATC TTGAATTCTGACTTTGGA 3' | 47% | 5' end of Msg P 0.6 kb from atg | 5'-652 <- -634 3' | Used for cloning Msg promoter. Bam HI bracketed |
| MSG3R (SEQ ID NO:13) | 31 | 5'[CGCGGATCCGCGC]TTG AATTCTGACTTTGGA3' | 45% | 5' end of Msg P 0.6 kb from atg | 5'-652 <- -634 3' | Used for cloning Msg promoter. Bam HI bracketed |
| MSG6Ratg (SEQ ID NO:14) | 37 | 5'[CGCGGATCCGCG]CATT CTTGAATTCAAATAATTG CAC3' | 54% | 3' end of Msg P including the atg | 5'-19 <- -1 3' | Used for cloning Msg promoter. Bam HI bracketed |
| MSG7R (SEQ ID NO:15) | 34 | 5'[CGCGGATCCGCG]TCTT GAATTCAAATAATTGCAC 3' | 53% | 3' end of Msg P excluding the atg | 5'-19 <- -1 3' | Used for cloning Msg promoter. Bam HI bracketed |
| MSGInFor (SEQ ID NO:16) | 29 | 5'[TACGTA]ATGGTAAGTT AAACTTAATAAAC3' | 76% | 5' end of Msg intron | 5' +188 -> +210 3' | Used for cloning the Msg intron. Sna BI bracketed. |
| MSGInRev (SEQ ID NO:17) | 28 | 5'[TACGTA]TGTCCCCTAC ATAATATTCAAC3' | 64% | 3' end of Msg intron | 5' +280 <- +301 3' | Used for cloning the Msg intron. Sna BI bracketed. |
| MSG3'UTR For (SEQ ID NO:18) | 32 | 5'[GAGCTC]TAAAATGATC CCTAAGTGGTTCACGC3' | 53% | 5' end of 3' UTR of Msg including stop codon | 5' +566- > +591 3' | Used for cloning the Msg 3' untranslated region. Sst I bracketed |
| MSG3'UTR Rev (SEQ ID NO:19) | 31 | 5'[GGAATTCC]GACAAACA AGGATAAATCCCCCT3' | 55% | 3' end of 3'UTR of Msg | 5' +843 <- +865 3' | Used for cloning the 3'UTR of Msg. EcoRI bracketed |

Abbreviations: MsgP = the promoter of Msg; UTR = untranslated region
Primer annealing numbers refer to Msg sequence unless otherwise specified.

TABLE 2B

The constructs used for promoter analysis

| Construct name | Size of fragment(s) (RE Sites omitted) | Primers | Position | Template | cloned into Backbone: |
|---|---|---|---|---|---|
| pBMA92atg | 1625 bp | MSG1F/MSG2Ratg SEQ ID NO:8/SEQ ID NO:12 | -2256—-634 (+ 3bp atg) | pMSG251 | pBI101 |
| pBMB103 | 1623 bp | MSG1F/MSG3R SEQ ID NO:8/SEQ ID NO:13 | -2256—-634 | PMSG251 | pBI101 |
| pBMC211atg | 1054 bp | MSG4F/MSG2Ratg SEQ ID NO:9/SEQ ID NO:12 | -1684—-634 (+ 3bp atg) | PMSG251 | pBI101 |
| pBMD162 | 1051 bp | MSG4F/MSG3 SEQ ID NO:9/SEQ ID NO:13 | -1684—-634 | PMSG251 | pBI101 |
| pBME178atg | 590 bp | MSG5F/MSG2Ratg SEQ ID NO:10/SEQ ID NO:12 | -1220—-634 (+ 3bp atg) | PMSG251 | pBI101 |
| pBMF219 | 587 bp | MSG5F/MSG3 SEQ ID NO:10/SEQ ID NO:13 | -1220—-634 | pMSG251 | pBI101 |
| pBMG305atg | 2259 bp | MSG1F/MSG6Ratg SEQ ID NO:8/SEQ ID NO:14 | -2256—+3 | MSG2 | pBI101 |
| pBMH358 | 2256 bp | MSG1F/MSG7 SEQ ID NO:8/SEQ ID NO:15 | -2256—-1 | MSG2 | pBI101 |
| pBM1372atg | 1687 bp | MSG4F/MSG6Ratg SEQ ID NO:9/SEQ ID NO:14 | -1684—+3 | MSG2 | pBI101 |
| pBMJ312 | 1684 bp | MSG4F/MSG7 SEQ ID NO:9/SEQ ID NO:15 | -1684—-1 | MSG2 | pBI101 |

TABLE 2B-continued

The constructs used for promoter analysis

| Construct name | Size of fragment(s) (RE Sites omitted) | Primers | Position | Template | cloned into Backbone: |
|---|---|---|---|---|---|
| pBMK340atg | 1223 bp | M5G5F/MSG6Ratg SEQ ID NO:10/SEQ ID NO:14 | −1220−+3 | MSG2 | pBI101 |
| pBML318 | 1220 bp | MSG5F/MSG7 SEQ ID NO:10/SEQ ID NO:15 | −1220−−1 | MSG2 | pBI101 |
| pBMM347atg | 655 bp | MSG8F/MSG6Ratg SEQ ID NO:11/SEQ ID NO:14 | −652−+3 | MSG2 | pBI101 |
| pBMN353 | 652 bp | MSG8F/MSG7 SEQ ID NO:11/SEQ ID NO:15 | −652−−1 | MSG2 | pBI101 |
| pBMU2 | 299 bp | MSG3'UTRFor/MSG3'UTRRev SEQ ID NO:18/SEQ ID NO:19 | +566−+865 | pMSG250 | pBI101 |
| pBMMU12 | 655 bp | MSG8F/MSG6Ratg SEQ ID NO:11/SEQ ID NO:14 | −652−+3 | MSG2 | pBI101 |
|  | 299 bp | MSG3'UTRFor/M5G3'UTRRev SEQ ID NO:18/SEQ ID NO:19 | +566−+865 | pMSG250 | pBI101 |
| PBMGU1 | 2259 bp | MSG1F/MSG6Ratg SEQ ID NO:8/SEQ ID NO:14 | −2256−+3 | MSG2 | pBI101 |
|  | 299 bp | MSG3'UTRFor/MSG3'UTRRev SEQ ID NO:18/SEQ ID NO:19 | +566−+865 | pMSG250 | pBI101 |
| pBMMIU32 | 655 bp | MSG8F/MSG6Ratg SEQ ID NO:11/SEQ ID NO:14 | −652−+3 | MSG2 | pBI101 |
|  | 113 bp | MSGInFor/MSGInRev SEQ ID NO:16/SEQ ID NO:17 | +188−+301 | pMSG250 | pBI101 |
|  | 299 bp | MSG3'UTRFor/MSG3'UTRRev SEQ ID NO:18/SEQ ID NO:19 | +566−+865 | pMSG250 | pBI101 |
| pBMGIU44 | 2259 bp | MSG1F/MSG6Ratg SEQ ID NO:8/SEQ ID NO:14 | −2256−+3 | MSG2 | pBI101 |
|  | 113 bp | MSGInFor/MSGInRev SEQ ID NO:16/SEQ ID NO:17 | +188−+301 | pMSG250 | pBI101 |
|  | 299 bp | MSG3'UTRFor/MSG3'UTRRev SEQ ID NO:18/SEQ ID NO:19 | +566−+865 | pMSG250 | pBI101 |
| pBMMInU11 | 655 bp | MSG8F/MSG6Ratg SEQ ID NO:11/SEQ ID NO:14 | −652−+3 | MSG2 | pBI101 |
|  | 113 bp (inv.) | MSGInFor/MSGInRev SEQ ID NO:16/SEQ ID NO:17 | +188−+301 | pMSG250 | pBI101 |
|  | 299 bp | MSG3'UTRFor/MSG3'UTRRev SEQ ID NO:18/SEQ ID NO:19 | +566−+865 | pMSG250 | pBI101 |

TABLE 3A

Pathogen Response in Transgenic Arabidopsis -- Vacuum infiltration

| Arabidopsis line: Pathogen: | G305atg: 7d | | M347: 9a | | pBI121:7 | | pBI101:6 | | Col-O | |
|---|---|---|---|---|---|---|---|---|---|---|
| P. syringae DC3000 avr+ | ni | + | ni | − | ni | + | ni | − | ni | − |
| P. syringae DC3000 avr− | ni | + | ni | − | ni | + | ni | − | ni | − |
| P. fluorescens 1855-344 | ni | + | ni | − | ni | + | ni | − | ni | − |
| BLANK (10 mM MgCl$_2$) | ni | + | ni | − | ni | + | ni | − | ni | − |

TABLE 3B

Hyper Sensitive Response -- Hand-inoculation

| Arabidopsis line: Pathogen: | G305atg:7d | | M347:9a | | pBI121:7 | | pBI101:6 | |
|---|---|---|---|---|---|---|---|---|
| P. syringae race 4 avr+ | ni | + | ni | − | ni | + | ni | − |
| P. syringae race 4 avr− | ni | + | ni | − | ni | + | ni | − |

The left sub-column indicates induction due to pathogens (ni=non-induced) and the right sub-column indicates the expected GUS expression seen as a result of developmental regulation. In Table 3A, four plants per pathogen and line combination were infiltrated and in Table 3B, 3 plants per construct and pathogen were hand-inoculated to test for hyper sensitive response. NOTE: avr+ carry pVSP288 and avr− carry pVSP61.

We claim:

1. A chimeric gene comprising a transcription regulatory sequence operably linked to a heterologous nucleic acid sequence wherein the transcription regulatory sequence comprises nucleotides 2941 to 3139 of SEQ ID NO:1, wherein said transcription regulatory sequence provides for preferential expression in the filament of a stamen.

2. A chimeric gene which is expressed in plants, said chimeric gene comprising an Msg transcription regulatory sequence and a DNA sequence which is heterologous to the Msg transcription regulatory sequence, wherein said DNA sequence which is heterologous to the Msg transcription regulatory sequence is operably linked to the Msg transcription regulatory sequence such that the chimeric gene is expressed in plants in at least one plant tissue which is a potential entry site for plant pathogens or a plant pest, wherein said at least one plant tissue is selected from the group consisting of pod, root, stem, node, shoot tips, flower, guard cell, nectary, petal, sepal, and short style tissue, and wherein the transcription regulatory sequence consists essentially of a nucleic acid selected from the group consisting of nucleotides 1055 to 1641 of SEQ ID NO:1; nucleotides 591 to 1641 of SEQ ID NO:1; nucleotides 19 to 1641 of SEQ ID NO:1; nucleotides 1623 to 2275 of SEQ ID NO:1; nucleotides 1055 to 2275 of SEQ ID NO:1; nucleotides 591 to 2275 of SEQ ID NO:1; nucleotides 19 to 2275 of SEQ ID NO:1; and nucleotides 1 to 2275 of SEQ ID NO:1.

3. The chimeric gene of claim 2, wherein the Msg transcription regulatory sequence consists essentially of nucleotides 1055 to 1641 of SEQ ID NO:1.

4. The chimeric gene of claim 2, wherein the Msg transcription regulatory sequence consists essentially of nucleotides 591 to 1641 of SEQ ID NO:1.

5. The chimeric gene of claim 2, wherein the Msg transcription regulatory sequence consists essentially of nucleotides 19 to 1641 of SEQ ID NO:1.

6. The chimeric gene of claim 2, wherein the Msg transcription regulatory sequence consists essentially of nucleotides 1623 to 2275 of SEQ ID NO:1.

7. The chimeric gene of claim 2, wherein the Msg transcription regulatory sequence consists essentially of nucleotides 1055 to 2275 of SEQ ID NO:1.

8. The chimeric gene of claim 2, wherein the Msg transcription regulatory sequence consists essentially of nucleotides 591 to 2275 of SEQ ID NO:1.

9. The chimeric gene of claim 2, wherein the Msg transcription regulatory sequence consists essentially of nucleotides 19 to 2275 of SEQ ID NO:1 or nucleotides 1 to 2275 of SEQ ID NO:1.

10. The chimeric gene of claim 2, wherein the heterologous DNA sequence is a sequence encoding a protein.

11. The chimeric gene of claim 10, wherein said protein is an antifungal protein, an antibacterial protein or an antiviral protein.

12. The chimeric gene of claim 10, wherein said protein is a chitinase protein.

13. The chimeric gene of claim 10, wherein said protein is a *Bacillus thuringiensis* insecticidal toxin protein.

14. A plant transformation vector comprising the chimeric gene of claim 2.

15. A method of directing expression of a nucleotide sequence in a plant organ which is a potential entry site for plant pathogens or plant pests, said method comprising the steps of:

(a) introducing into a plant cell or plant tissue the chimeric gene of claim 2, (b) selecting a transformed plant cell or transformed plant tissue comprising said chimeric gene;

(c) regenerating a transformed plant from said transformed plant cell or said transformed plant tissue;

(d) growing the transformed plant or a seed or progeny thereof, wherein the seed or progeny thereof comprises the chimeric gene, whereby the chimeric gene is expressed in a potential entry site for plant pathogens or plant pests in said transformed plant.

16. The method of claim 15, wherein the Msg transcription regulatory sequence consists essentially of nucleotides 1055 to 1641 of SEQ ID NO:1.

17. The method of claim 15, wherein the Msg transcription regulatory sequence consists essentially of nucleotides 591 to 1641 of SEQ ID NO:1.

18. The method of claim 15, wherein the Msg transcription regulatory sequence consists essentially of nucleotides 19 to 1641 of SEQ ID NO:1.

19. The method of claim 15, wherein the Msg transcription regulatory sequence consists essentially of nucleotides 1623 to 2275 of SEQ ID NO:1.

20. The method of claim 15, wherein the Msg transcription regulatory sequence consists essentially of nucleotides 1055 to 2275 of SEQ ID NO:1.

21. The method of claim 15, wherein the Msg transcription regulatory sequence consists essentially of nucleotides 591 to 2275 of SEQ ID NO:1.

22. The method of claim 15, wherein the Msg transcription regulatory sequence consists essentially of nucleotides 19 to 2275 of SEQ ID NO:1.

23. The method of claim 15, wherein the heterologous DNA sequence is a sequence encoding a protein.

24. The method of claim 23, wherein said protein is an antifungal protein, an antibacterial protein or an antiviral protein.

25. The method of claim 24, wherein said protein is a chitinase protein.

26. The chimeric gene of claim 24, wherein said protein is a *Bacillus thuringiensis* insecticidal toxin protein.

27. A transgenic plant comprising within its genome a chimeric gene which is expressed in plants, wherein said chimeric gene comprises an Msg transcription regulatory sequence and a DNA sequence which is heterologous to the Msg transcription regulatory sequence, wherein said DNA sequence which is heterologous to the Msg transcription regulatory sequence is operably linked to the Msg transcription regulatory sequence, such that the chimeric gene is expressed in plants in at least one plant tissue which is a potential entry site for plant pathogens or a plant pest, wherein said at least one plant tissue is selected from the group consisting of pod, root, stem, node, shoot tips, flower, guard cell, nectary, petal, sepal, and short style tissue, and wherein the transcription regulatory sequence consists essentially of a nucleic acid selected from the group consisting of nucleotides 1055 to 1641 of SEQ ID NO:1, nucleotides 591 to 1641 of SEQ ID NO:1; nucleotides 19 to 1641 of SEQ ID NO:1; nucleotides 1623 to 2275 of SEQ ID NO:1; nucleotides 1055 to 2275 of SEQ ID NO:1; nucleotides 591 to 2275 of SEQ ID NO:1; nucleotides 19 to 2275 of SEQ ID NO:1; and nucleotides 1 to 2275 of SEQ ID NO:1.

28. The transgenic plant of claim 27, wherein the Msg transcription regulatory sequence consists essentially of nucleotides 1055 to 1641 of SEQ ID NO:1.

29. The transgenic plant of claim 27, wherein the Msg transcription regulatory sequence consists essentially of nucleotides 591 to 1641 of SEQ ID NO:1.

30. The transgenic plant of claim 27, wherein the Msg transcription regulatory sequence consists essentially of nucleotides 19 to 1641 of SEQ ID NO:1.

31. The transgenic plant of claim 27, wherein the Msg transcription regulatory sequence consists essentially of nucleotides 1623 to 2275 of SEQ ID NO:1.

32. The transgenic plant of claim 27, wherein the Msg transcription regulatory sequence consists essentially of nucleotides 1055 to 2275 of SEQ ID NO:1.

33. The transgenic plant of claim 27, wherein the Msg transcription regulatory sequence consists essentially of nucleotides 591 to 2275 of SEQ ID NO:1.

34. The transgenic plant of claim 27, wherein the Msg transcription regulatory sequence consists essentially of nucleotides 19 to 2275 of SEQ ID NO:1.

35. The transgenic plant of claim 27, wherein the Msg transcription regulatory sequence consists essentially of nucleotides 1 to 2275 of SEQ ID NO:1.

36. The transgenic plant of claim 27, wherein said protein is an antifungal protein, an antibacterial protein or an antiviral protein.

37. The transgenic plant of claim 36, wherein said protein is a chitinase protein.

38. The transgenic plant of claim 36, wherein said protein is a *Bacillus thuringiensis* insecticidal toxin protein.

39. The transgenic plant of claim 27, wherein said plant is a monocotyledonous plant.

40. The transgenic plant of claim 27, wherein said plant is a dicotyledonous plant.

41. The transgenic plant of claim 40, wherein said plant is a member of the Leguminaceae.

42. The transgenic plant of claim 41, wherein said plant is a species of Glycine.

43. The transgenic plant of claim 41, wherein said plant is a species of Phaseolus.

44. The transgenic plant of claim 40, wherein said plant is a member of the Solanaceae.

45. The transgenic plant of claim 44, wherein said plant is *Lysopersicon esculentum.*

* * * * *

UNITED STATES PATENT AND TRADEMARK OFFICE
CERTIFICATE OF CORRECTION

PATENT NO.     : 6,573,428 B1
DATED          : June 3, 2003
INVENTOR(S)    : Vodkin et al.

It is certified that error appears in the above-identified patent and that said Letters Patent is hereby corrected as shown below:

Drawings,
Fig. 2, replace "HincIII" with -- HincII -- in the upper part of the figure.
Fig. 8 throughout, replace "at" with -- atg --.

Column 3,
Line 61, delete "Hin dIII" and replace with -- Hind III --.

Column 4,
Line 14, delete "Hin dIII" and replace with -- Hind III --.

Column 5,
Line 1, delete "I-DNA" and replace with -- T-DNA --.

Column 6,
Line 10, delete "VS-i107" and replace with -- VS-107 --.

Column 9,
Line 63, "XpBMMIU32" and replace with -- pBMMIU32 --.

Figure 10:
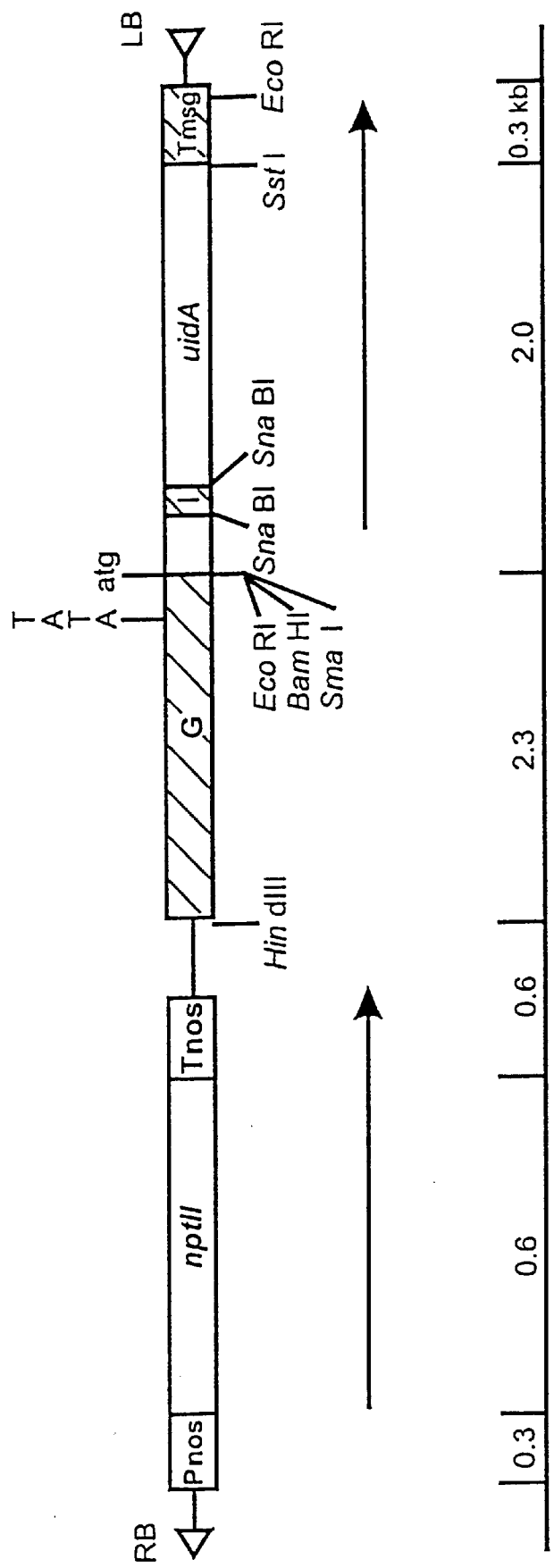
FIG. 10: Schematic of the I-DNA region of pBMGIU44.

Column 10,
Line 59, delete "FIGS.8A-8E" and replace with -- FIGS.9A-9E --.
Line 61, delete "FIG.9" and replace with -- FIG.10 --.

Column 11,
Line 9, delete the period "." between "not" and "show".
Line 27, delete "intron constructs express".

Column 18,
Line 50, delete "3389-3402/When" and replace with -- 3389-3401. When --.
Line 60, delete the bracket following "sequence".

Column 22,
Line 49, insert -- that -- between "cassette" and "can".

Column 23,
Line 37, delete "expressing -in" and replace with -- expressed in --.

UNITED STATES PATENT AND TRADEMARK OFFICE
CERTIFICATE OF CORRECTION

PATENT NO. : 6,573,428 B1
DATED : June 3, 2003
INVENTOR(S) : Vodkin et al.

It is certified that error appears in the above-identified patent and that said Letters Patent is hereby corrected as shown below:

<u>Column 30,</u>
Line 19, delete "god" and replace with -- pod --.

<u>Column 31,</u>
Line 39, delete "FIG.8" and replace with -- FIG.9 --.
Line 40, delete "FIG.9" and replace with -- FIG.10 --.

<u>Column 32,</u>
Line 39, delete "pBMG3 05" and replace with -- pBMG305 --.

<u>Column 33,</u>
Line 31, delete "o 1 $\mu$m" and replace with -- $\varnothing$ 1 $\mu$m --.

<u>Column 35,</u>
Line 5, delete "(lug)" and replace with -- (1 $\mu$g) --.
Line 27, delete "min" and replace with -- $\text{min}^{-1}$ --.

<u>Column 41,</u>
Table 2B, first column, second entry, delete "pBMB103" and replace with
-- pBMBI03 --.
Table 2B, first column, last entry, delete "pBMJ312" and replace with -- pBMI312 --.

Signed and Sealed this

Thirtieth Day of December, 2003

JAMES E. ROGAN
*Director of the United States Patent and Trademark Office*